United States Patent
Griffith et al.

(10) Patent No.: US 7,166,433 B2
(45) Date of Patent: Jan. 23, 2007

(54) TRANSDUCTIN-1 AND TRANSDUCTIN-2 AND APPLICATIONS TO HEREDITARY DEAFNESS

(75) Inventors: Andrew J. Griffith, Rockville, MD (US); Kiyoto Kurima, Gaithersburg, MD (US); Edward Wilcox, Gaithersburg, MD (US); Thomas Friedman, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 253 days.

(21) Appl. No.: 10/792,307

(22) Filed: Mar. 3, 2004

(65) Prior Publication Data

US 2005/0196759 A1   Sep. 8, 2005

(51) Int. Cl.
C12Q 1/68 (2006.01)
C12N 1/21 (2006.01)
C12N 1/19 (2006.01)
C12N 15/63 (2006.01)
C12N 5/10 (2006.01)
A61K 31/7072 (2006.01)
C07H 21/04 (2006.01)

(52) U.S. Cl. .................. 435/6; 435/252.3; 435/254.11; 435/320.1; 435/325; 435/348; 514/44; 536/23.5

(58) Field of Classification Search ...................... None
See application file for complete search history.

(56) References Cited

U.S. PATENT DOCUMENTS 6,040,138 A   3/2000 Lockhart et al.
6,197,506 B1  3/2001 Fodor et al.
6,485,908 B1  11/2002 Petit et al.

FOREIGN PATENT DOCUMENTS

WO   WO 98/00014 A1   1/1998
WO   WO 99/09210 A2   2/1999
WO   WO 01/75067 A2 * 10/2001
WO   WO 02/068579 A2 * 9/2002

OTHER PUBLICATIONS

Corey et al., " Ionic Basis of the Receptor Potential in a Vertebrate Hair Cell," *Nature*, vol. 281, pp. 675-677 (1979).
Hudspeth et al., "Sensitivity, Polarity, and Conductance Change in the Response of Vertebrate Hair Cells to Controlled Mechanical Stimuli," *Proc. Natl. Acad. Sci. USA*, vol. 74 (6), pp. 2407-2411 (1977).
Jain et al., "A Human Recessive Neurosensory Nonsyndromic Hearing Impairment Locus is a Potential Homologue of the Murine Deafness (*dn*) Locus," *Hum. Mol. Genet.*, vol. 4 (12), pp. 2391-2394 (1995).
Kurima et al., "Genetic Map Localization of DFNA34 and DFNA26, Two Autosomal Dominant Non-Syndromic Deafness Loci," *Am. J. Hum. Genet.*, vol. 67, p. 300, Poster No. 1654 (2000).
Kurima, et al., "Dominant and Recessive Deafness Caused by Mutations of a Novel Gene, TMC1, Required for Cochlear Hair-Cell Function," *Nat. Genet.*, vol. 30, pp. 277-284 (2002).
Scott et al., "Refining the DFNB7-DFNB11 Deafness Locus Using Intragenic Polymorphisms in a Novel Gene, *TMEM2*," *Gene*, vol. 246, pp. 265-274 (2000).

* cited by examiner

*Primary Examiner*—Robert A. Wax
(74) *Attorney, Agent, or Firm*—Leydig, Voit & Mayer, Ltd.

(57) ABSTRACT

The invention provides an isolated or purified nucleic acid molecule consisting essentially of the nucleotide sequence encoding transductin-2 (TDC2), related and derivative nucleic acid molecules, vectors comprising the isolated or purified nucleic acid sequences, cells comprising such vectors, polypeptides encoded by the nucleic acid molecules, monoclonal antibodies and cell lines producing the monoclonal antibodies. The invention also provides methods of treating, prognosticating and monitoring hearing loss.

28 Claims, No Drawings

TRANSDUCTIN-1 AND TRANSDUCTIN-2 AND APPLICATIONS TO HEREDITARY DEAFNESS

FIELD OF THE INVENTION

The present invention pertains to isolated or purified nucleic acids encoding transductin-1 (TDC1; now referred to as transmembrane cochlear-expressed gene 1 (TMC-1)), transductin-2 (TDC2; now referred to as transmembrane cochlear-expressed gene 2 (TMC2)), and fragments thereof, a vector comprising such a nucleic acid, a cell comprising such a vector, an isolated or purified polypeptide, a monoclonal antibody-producing cell line, a monoclonal antibody, pharmaceutically acceptable compositions of the above nucleic acids and polypeptides, and methods of diagnosis, prognosis and treatment of hearing loss, particularly DFNA 36 and DFNB 7/11-linked hearing loss.

BACKGROUND OF THE INVENTION

Hearing loss is a common communication disorder. Congenital hearing impairment occurs in approximately 1 in 1,000 children born in the United States. See Jain et al., A human recessive neurosensory nonsyndromic hearing impairment locus is a potential homologue of the murine deafness (dn) locus, *Human Molecular Genetics* 4(12): 2391–2394 (1995); and Scott et al., Refining the DFNB7-DFNB11 deafness locus using intragenic polymorphisms in a novel gene, TMEM2, *Gene* 246: 265–274 (2000). One to two percent of graduates of neonatal intensive care units also suffer such hearing impairment. See Jain et al. (1995), supra. Nearly 1 in 2 adults have functionally significant hearing loss by the eighth decade of life.

Deafness can be caused by a number of environmental and disease-related factors. In developed countries, however, at least 50% of the cases of deafness are inherited. See Scott et al. (2000), supra. Factors associated with an increased risk for hearing loss include male gender, exposure to aminoglycoside antibiotics, exposure to noise, head trauma, and barotraumas. The majority of cases seem to involve single gene mutations, as there is no additional clinical anomaly, and an autosomal recessive mode of inheritance predominates. Nonsyndromic hereditary hearing impairment (NSHHI) is considered to be highly heterogeneous, and is thought to be caused by a large number of genes.

Vertebrates detect sounds, body accelerations and water movements with the acoustico-lateralis sensory system (Hudspeth et al., Sensitivity, polarity, and conductance change in the response of vertebrate hair cells to controlled mechanical stimuli, *Proc. Natl. Acad. Sci. USA* 74(6): 2407–2411 (1977)). The primary receptors of this system are neuroepithelial cells termed hair cells. Each of these cells has a "hair bundle" on its apical surface, which is comprised of an elongated microvillus (stereocilium) and, in most cases, a single true cilium (kinocilium). Vibrations, such as from sound waves, stimulate the cells by bending the hair bundles. Bending of the hair bundles leads to the production of a small receptor potential, which excites afferent nerve fibers by chemical or electrical synapses. The exact mechanism of the production of the potential is not yet known, with the existence of conflicting data as to the ions involved in creating the potential (Corey et al., Ionic basis of the receptor potential in a vertebrate hair cell, *Nature* 281: 675–77 (1979)).

Thus far, linkage studies have been the primary method employed to identify potential loci implicated in hereditary deafness. However, single families suitable in size for conventional linkage analysis are not common. NSHHI also lends itself poorly to subclassification by audiometric criteria. Thus, traditional studies have used consanguineous families from geographically isolated populations to map several different loci which are associated with recessive NSHHI (Jain et al. (1995), supra). In humans certain forms of NSHHI have been found to localize to a region of chromosome 9. See, e.g. Kurima et al., Genetic map localization of DFNA34 and DFNA36, two novel autosomal dominant nonsyndromic deafness loci, *ARO Abstracts* 24:265 (2001); and Scott et al. (2000), supra. Scott et al. identified a gene in the relevant region of the chromosome; however, it was poorly correlated to hearing loss at the particular locus, as the protein was expressed in a variety of other tissues, such as the heart, brain, spleen, lung, liver, muscle and kidney, and no difference in transcript size or expression level was apparent between normal and deaf mice by Northern blot analysis.

In view of the above, it is an object of the present invention to provide a gene that correlates well with hearing loss as well as the encoded polypeptide and related vectors, host cells, polypeptides, antibodies, antibody-producing cell lines and methods of diagnosing, prognosticating and treating hearing loss. These and other objects and advantages of the present invention, as well as additional inventive features, will be apparent from the description of the invention provided herein.

BRIEF SUMMARY OF THE INVENTION

The present invention provides an isolated or purified nucleic acid molecule consisting essentially of a nucleotide sequence encoding TDC2 or a fragment thereof comprising at least 110 contiguous nucleotides, and an isolated or purified nucleic acid molecule consisting essentially of a nucleotide sequence that is complementary to a nucleotide sequence encoding human TDC2 or a fragment thereof.

Also provided by the present invention is a vector comprising one of the above-described isolated or purified nucleic acid molecules. Further provided is a cell comprising one of the above-identified nucleic acid molecules. Also provided is a composition comprising one of the above identified isolated or purified nucleic acid molecules or vectors and a pharmaceutically acceptable carrier.

An isolated or purified polypeptide molecule consisting essentially of an amino acid sequence encoding TDC2 or a fragment thereof comprising at least 71 contiguous amino acids, which is optionally glycoslyated, amidated, carboxylated, phosphorylated, esterified, N-acylated or converted into an acid addition salt, is further provided.

Also provided is a composition comprising an above-described isolated or purified polypeptide molecule and a pharmaceutically acceptable carrier. Further provided is a cell line that produces a monoclonal antibody that is specific for an above-described isolated or purified polypeptide molecule. Still further provided is the antibody produced by the above-mentioned cell-line.

A method of detecting hearing loss or a predisposition to hearing loss in an animal also is provided. The method comprises detecting at least one mutation in a gene encoding TDC2 in a test sample comprising a nucleic acid comprising the TDC2 gene obtained from the animal, wherein the at least one mutation is indicative of hearing loss or a predisposition to hearing loss in the animal.

Further provided is a method of determining the level of nucleic acid comprising the wild-type TDC2 gene and/or a mutant TDC2 gene in a test sample comprising a nucleic acid comprising the wild-type TDC2 gene and/or a mutant TDC2 gene obtained from an animal. The method comprises assaying the test sample for the level of nucleic acid comprising the wild-type TDC2 gene and/or a mutant TDC2 gene, wherein a decrease in the level of nucleic acid comprising the wild-type TDC2 gene and/or an increase in the level of nucleic acid comprising a mutant TDC2 gene in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

A method for detecting hearing loss or a predisposition to hearing loss in an animal also is provided. The method comprises detecting a mutant TDC2 in a test sample comprising protein comprising TDC2 obtained from the animal, wherein the presence of a mutant TDC2 in the test sample is indicative of hearing loss or a predisposition to hearing loss in the animal.

Also provided is a method of determining the level of wild-type TDC2 and/or a mutant TDC2 in a test sample comprising protein comprising wild-type TDC2 and/or a mutant TDC2 obtained from an animal. The method comprises assaying the test sample for the level of wild-type TDC2 and/or a mutant TDC2, wherein a decrease in the level of wild-type TDC2 and/or an increase in the level of a mutant TDC2 in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

The invention still further provides a method of treating an animal prophylactically or therapeutically for hearing loss, wherein the hearing loss is due to a complete or partial loss of wild-type TDC2, which method comprises providing TDC2 to the animal, whereupon the animal is treated prophylactically or therapeutically for hearing loss. The TDC2 can be provided to the animal by administering to the animal a nucleic acid encoding and expressing wild-type TDC2. The TDC2 also can be provided to the animal by administering to the animal the wild-type TDC2 protein.

Further provided is a method of identifying one or more agents which interact with a TDC2 gene in a cell, comprising administering one or more agents to the cell comprising the TDC2 gene and assaying the expression level of the TDC2 gene by the cell, wherein an increase or decrease in the expression level of TDC2 gene is indicative of an interaction between one or more agents and the TDC2 gene in the cell.

DETAILED DESCRIPTION OF THE INVENTION

The TDC1 and TDC2 genes are implicated in DFNA 36- and DFNB 7/11-linked hearing loss, two forms of hereditary deafness. These genes also may be, at least in part, the cause of certain forms of non-hereditary deafness, or other forms of hereditary deafness. These genes encode a mechanotransduction channel of an animal hair cell, particularly hair cells of the inner ear. These cells are responsible for turning mechanical stimulation (such as sound waves) into chemical signals which can be processed by the brain. Any abnormality in the normal expression of this mechanotransduction channel can lead to hearing loss. This abnormal expression may result from mutations or deletions in the sequence or in the sequences surrounding the particular gene, or from other genetic abnormalities as are known in the art. Particularly, the mutation(s) can compromise the ability of the TDC1 and/or TDC2 gene product to form a component of a hair cell of the inner ear of the animal, thereby causing hearing loss. The mutation(s) can also compromise the ability of the TDC1 and/or TDC2 gene product to form all or some of an ion transduction channel of the hair cell of the inner ear of the animal. Further, the mutation(s) can compromise the mechanosensory activity of the TDC1 and/or TDC2 gene product. Hearing loss can mean either the entire loss or partial loss of hearing as would be understood by an ordinarily skilled artisan. The hearing loss can be hereditary, sensorineural hearing loss, nonsyndromic autosomal-dominant hearing loss, and/or DFNA 36- or DFNB 7/11-linked hearing loss.

Mutations in TDC1 and/or TDC2 can cause deafness. In particular, dominant mutations can cause childhood-onset, rapidly progressive, bilateral sensorineural hearing loss. Several recessive mutations can cause congenital, profound bilateral sensorineural deafness. Several of the recessive mutations can also result in functional null alleles: nonsense mutations, genomic deletion of two exons, or frameshift mutations.

Any animal with hair cells within their auditory receptor can benefit from the present invention. Desirably, the animal is a mammal, preferably a human. However, animals such as birds, especially chickens, also can benefit from the present invention.

The present invention provides an isolated or purified nucleic acid molecule consisting essentially of a nucleotide sequence encoding transductin or a fragment thereof. By transductin is meant TDC1 and/or TDC2, preferably of an animal, and even more preferably of a human. By "isolated" is meant the removal of transductin from its natural environment. By "purified" is meant that transductin, whether it has been removed from nature or synthesized and/or amplified under laboratory conditions, has been increased in purity, wherein "purity" is a relative term, not "absolute purity." "Nucleic acid molecule" is intended to encompass a polymer of DNA or RNA, i.e., a polynucleotide, which can be single-stranded or double-stranded and which can contain non-natural or altered nucleotides. Moreover, the nucleic acids and genes can comprise exons, introns, and/or regulatory regions and elements.

Preferably, the isolated or purified nucleic acid molecule consists essentially of a nucleotide sequence encoding TDC1 or a fragment thereof comprising at least 314 contiguous nucleotides. The TDC1 can be a human TDC1. In a preferred embodiment, the isolated or purified nucleic acid molecule can encode the amino acid sequence of SEQ ID NO: 2 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, the isolated or purified nucleic acid molecule consists essentially of the nucleotide sequence of SEQ ID NO: 1 or a fragment thereof comprising at least 314 contiguous nucleotides. More preferably, the fragment comprises at least 320 contiguous nucleotides. Still more preferably, the fragment comprises at least 330 contiguous nucleotides. Even more preferably, the fragment comprises at least 340 contiguous nucleotides. Further, the isolated or purified nucleic acid molecule can hybridize under moderately stringent conditions to an isolated or purified nucleic acid molecule consisting essentially of the nucleotide sequence that is complementary to SEQ ID NO: 1 or a fragment thereof, such as naturally occurring and artificially generated variants. Alternatively, but still preferably, the isolated or purified nucleic acid molecule can share 43% or more identity with SEQ ID NO: 1, such as naturally occurring and artificially generated variants. Also preferably, the isolated or purified nucleic acid molecule can share 50% or more identity with SEQ ID NO: 1. More preferably, the isolated or purified nucleic acid molecule can share 70% or more identity with SEQ ID NO: 1. Still more preferably, the isolated or purified nucleic acid molecule can share 90% or more identity with SEQ ID NO: 1.

Alternatively, the isolated or purified nucleic acid molecule can encode the amino acid sequence of SEQ ID NO: 6 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, the isolated or purified nucleic acid molecule consists essentially of the nucleotide sequence of SEQ ID NO: 5 or a fragment thereof comprising at least 314 contiguous nucleotides. More preferably, the fragment comprises at least 320 contiguous nucleotides. Still more preferably, the fragment comprises at least 330 contiguous nucleotides. Even more preferably, the fragment comprises at least 340 contiguous nucleotides. Further, the isolated or purified nucleic acid molecule can hybridize under moderately stringent conditions to an isolated or purified nucleic acid molecule consisting essentially of the nucleotide sequence that is complementary to SEQ ID NO: 5 or a fragment thereof, such as naturally occurring and artificially generated variants. Alternatively, but still preferably, the isolated or purified nucleic acid molecule can share 40% or more identity with SEQ ID NO: 5, such as naturally occurring and artificially generated variants. Also preferably, the isolated or purified nucleic acid molecule can share 45% or more identity with SEQ ID NO: 5. More preferably, the isolated or purified nucleic acid molecule can share 60% or more identity with SEQ ID NO: 5. Still more preferably, the isolated or purified nucleic acid molecule can share 80% or more identity with SEQ ID NO: 5.

Also preferably, the isolated or purified nucleic acid molecule consists essentially of a nucleotide sequence encoding TDC2 or a fragment thereof comprising at least 110 contiguous nucleotides. The TDC2 can be a human TDC2. In a preferred embodiment, the isolated or purified nucleic acid molecule can encode the amino acid sequence of SEQ ID NO: 4 or a fragment thereof comprising at least 70 contiguous amino acids. More preferably, the fragment comprises at least 75 contiguous amino acids. Still more preferably, the fragment comprises at least 80 contiguous amino acids. Even more preferably, the fragment comprises at least 85 contiguous amino acids. Alternatively, the isolated or purified nucleic acid molecule consists essentially of the nucleotide sequence of SEQ ID NO: 3 or a fragment thereof comprising at least 110 contiguous nucleotides. More preferably, the fragment comprises at least 115 contiguous nucleotides. Still more preferably, the fragment comprises at least 130 contiguous nucleotides. Even more preferably, the fragment comprises at least 150 contiguous nucleotides. In a further preferred embodiment, the isolated or purified nucleic acid molecule can hybridize under moderately stringent conditions to an isolated or purified nucleic acid molecule consisting essentially of the nucleotide sequence that is complementary to SEQ ID NO: 3 or a fragment thereof. Alternatively, but still preferably, the isolated or purified nucleic acid molecule can share 49% or more identity with SEQ ID NO: 3. Also preferably, the isolated or purified nucleic acid molecule can share 55% or more identity with SEQ ID NO: 3. More preferably, the isolated or purified nucleic acid molecule can share 70% or more identity with SEQ ID NO: 3. Still more preferably, the isolated or purified nucleic acid molecule can share 90% or more identity with SEQ ID NO: 3.

Alternatively, but still preferably, the isolated or purified nucleic acid molecule can encode the amino acid sequence of SEQ ID NO:8 or a fragment thereof comprising at least 71 contiguous amino acids. Also preferably, the isolated or purified nucleic acid molecule can consist essentially of the nucleotide sequence of SEQ ID NO: 7 or a fragment thereof comprising at least 110 contiguous nucleotides. More preferably, the fragment comprises at least 115 contiguous nucleotides. Still more preferably, the fragment comprises at least 120 contiguous nucleotides. Even more preferably, the fragment comprises at least 125 nucleotides. In a further preferred embodiment, the fragment can hybridize under moderately stringent conditions to an isolated or purified nucleic acid molecule consisting essentially of the nucleotide sequence that is complementary to SEQ ID NO: 7 or a fragment thereof. In an alternative embodiment, the isolated or purified nucleic acid molecule can share 41% or more identity with SEQ ID NO: 7. Alternatively, but still preferably, the isolated or purified nucleic acid molecule can share 55% or more identity with SEQ ID NO: 7. More preferably, the isolated or purified nucleic acid molecule can share 75% or more identity with SEQ ID NO: 7. Still more preferably, the isolated or purified nucleic acid molecule can share 90% or more identity with SEQ ID NO: 7.

An isolated or purified nucleic acid molecule consisting essentially of a nucleotide sequence encoding a variant TDC1 or a fragment thereof can comprise one or more insertions, deletions, inversions and/or substitutions. Desirably, the variant TDC1 does not differ functionally from the corresponding unmodified TDC1 or a fragment thereof comprising at least 314 contiguous nucleotides, such as that comprising SEQ ID NO: 1. Preferably, the one or more substitution(s) results in the substitution of an amino acid of the encoded TDC1 with another amino acid of approximately equivalent mass, structure and charge.

An isolated or purified nucleic acid molecule consisting essentially of a nucleotide sequence encoding a variant TDC2 or a fragment thereof can comprise one or more insertions, deletions, inversions and/or substitutions. Desirably, the variant TDC2 does not differ functionally from the corresponding unmodified TDC2 or a fragment thereof comprising at least 110 contiguous nucleotides, such as that comprising SEQ ID NO: 3. Preferably, the one or more substitution(s) results in the substitution of an amino acid of the encoded TDC2 with another amino acid of approximately equivalent mass, structure and charge.

The present invention also provides an isolated or purified nucleic acid molecule consisting essentially of a nucleotide sequence that is complementary to a nucleotide sequence encoding human TDC1 or a fragment thereof. Such an isolated or purified nucleic acid molecule preferably is complementary to a nucleotide sequence encoding the amino acid sequence of SEQ ID NO: 2 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, but still preferably, the isolated or purified nucleic acid molecule is complementary to the nucleotide sequence of SEQ ID NO: 1 or a fragment thereof comprising at least 314 contiguous nucleotides. In another preferred embodiment, the isolated or purified nucleic acid molecule hybridizes under moderately stringent conditions to an isolated or purified nucleic acid molecule consisting essentially of SEQ ID NO: 1 or a fragment thereof. Preferably, the isolated or purified nucleic acid molecule shares 43% or more identity with the nucleotide sequence that is complementary to SEQ ID NO: 1. More preferably, the isolated or purified nucleic acid molecule shares 50% or more identity with SEQ ID NO: 1. Even more preferably, the isolated or purified nucleic acid molecule shares 70% or more sequence identity with SEQ ID NO: 1. Still more preferably, the isolated or purified nucleic acid molecule shares 90% or more sequence identity with SEQ ID NO: 1. An isolated or purified nucleic acid molecule consisting essentially of a nucleotide sequence that is complementary to either of a nucleotide sequence encoding a variant TDC1 or a fragment thereof also can be obtained.

The present invention also provides an isolated or purified nucleic acid molecule consisting essentially of a nucleotide sequence that is complementary to either of a nucleotide sequence encoding human TDC2 or a fragment thereof. Such an isolated or purified nucleic acid molecule preferably is complementary to a nucleotide sequence encoding the amino acid sequence of SEQ ID NO: 4 or a fragment thereof comprising at least 70 contiguous amino acids. More preferably, the fragment comprises at least 75 contiguous amino acids. Still more preferably, the fragment comprises at least 80 contiguous amino acids. Even more preferably, the fragment comprises at least 85 contiguous amino acids. Alternatively, but still preferably, the isolated or purified nucleic acid molecule is complementary to the nucleotide sequence of SEQ ID NO: 3 or a fragment thereof comprising at least 110 contiguous nucleotides. In another preferred embodiment, the isolated or purified nucleic acid molecule hybridizes under moderately stringent conditions to an isolated or purified nucleic acid molecule consisting essentially of SEQ ID NO: 3 or a fragment thereof. Preferably, the isolated or purified nucleic acid molecule shares 49% or more identity with the nucleotide sequence that is complementary to SEQ ID NO: 3. More preferably, the isolated or purified nucleic acid molecule shares 55% or more identity with SEQ ID NO: 3. Even more preferably, the isolated or purified nucleic acid molecule shares 75% or more sequence identity with SEQ ID NO: 3. Still more preferably, the isolated or purified nucleic acid molecule shares 90% or more sequence identity with SEQ ID NO: 3. An isolated or purified nucleic acid molecule consisting essentially of a nucleotide sequence that is complementary to either of a nucleotide sequence encoding a variant TDC2 or a fragment thereof also can be obtained.

Whereas embodiments of the present invention are described in the context of applications to humans, the teachings set forth herein can be adapted to other animals as a matter of routine experimentation. For example, further disclosed herein are the sequences for a mouse TDC1 (SEQ ID NOS: 5 (nucleic acid) and 6 (amino acid)) and a mouse TDC2 (SEQ ID NOS: 7 (nucleic acid) and 8 (amino acid)). These sequences also can be used in the context of the present invention and constitute alternative preferred embodiments.

With respect to the above, one of ordinary skill in the art knows how to generate insertions, deletions, inversions and/or substitutions in a given nucleic acid molecule. See, for example, the references cited herein under "Example." It is preferred that the one or more substitution(s) result(s) in the substitution of an amino acid with another amino acid of approximately equivalent mass, structure and charge.

Also with respect to the above, "does not differ functionally from" is intended to mean that the variant transductin has activity characteristic of the unmodified transductin. In other words, it regulates a transductin-responsive gene. However, the variant transductin can be more or less active than the unmodified transductin as desired in accordance with the present invention.

An indication that polynucleotide sequences are substantially identical is if two molecules selectively hybridize to each other under moderately stringent conditions. The phrase "hybridizes to" refers to the selective binding of a single-stranded nucleic acid probe to a single-stranded target DNA or RNA sequence of complementary sequence when the target sequence is present in a preparation of heterogeneous DNA and/or RNA. "Moderately stringent conditions" are sequence-dependent and will be different in different circumstances. Generally, moderately stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

For example, under moderately stringent conditions, as that term is understood by one skilled in the art, hybridization is preferably carried out using a standard hybridization buffer at a temperature ranging from about 50° C. to about 75° C., even more preferably from about 60° C. to about 70° C., and optimally from about 65° C. to about 68° C. Alternately, formamide can be included in the hybridization reaction, and the temperature of hybridization can be reduced to preferably from about 35° C. to about 45° C., even more preferably from about 40° C. to about 45° C., and optimally to about 42° C. Desirably, formamide is included in the hybridization reaction at a concentration of from about 30% to about 50%, preferably from about 35% to about 45%, and optimally at about 40%. Moreover, optionally, the hybridized sequences are washed (if necessary to reduce non-specific binding) under relatively highly moderately stringent conditions, as that term is understood by those skilled in the art. For instance, desirably, the hybridized sequences are washed one or more times using a solution comprising salt and detergent, preferably at a temperature of from about 50° C. to about 75° C., even more preferably at from about 60° C. to about 70° C., and optimally from about 65° C. to about 68° C. Preferably, a salt (e.g., such as sodium chloride) is included in the wash solution at a concentration of from about 0.01 M to about 1.0 M. Optimally, a detergent (e.g., such as sodium dodecyl sulfate) is also included at a concentration of from about 0.01% to about 1.0%.

The following are examples of highly stringent and moderately stringent conditions for a Southern hybridization in aqueous buffers (no formamide) (Sambrook and Russell, *Molecular Cloning*, 3rd Ed. SCHL Press (2001)):

| Highly stringent hybridization conditions: | Moderately Stringent hybridization conditions: |
|---|---|
| 6 × SSC or 6 × SSPE 5 × Denhardt's Reagent 1% SDS 100 μg/ml salmon sperm DNA hybridization at 65–68° C. | 6 × SSC or 6 × SSPE 5 × Denhardt's Reagent 1% SDS 10 μg/ml salmon sperm DNA hybridization at 58–64° C. |
| Highly stringent washing conditions: | Moderately stringent washing conditions: |
| 0.1 × SSC/0.1% SDS washing at 65–68° C. | 2 × SSC/0.1% SDS washing at 58–64° C. |

In view of the above, "stringent conditions" preferably allow for about 20% mismatch, more preferably up to about 15% mismatch, and most preferably up to about 5% mismatch, such as 4%, 3%, 2%, or 1% mismatch. "At least moderately stringent conditions" preferably allow for up to about 40% mismatch, more preferably up to about 30% mismatch, and most preferably up to about 20% mismatch. "Low stringency conditions" preferably allow for up to about 60% mismatch, more preferably up to about 50% mismatch, and most preferably up to about 40% mismatch. With respect to the preceding ranges of mismatch, 1% mismatch corresponds to one degree decrease in the melting temperature.

The above isolated or purified nucleic acid molecules also can be characterized in terms of "percentage of sequence identity." In this regard, a given nucleic acid molecule as described above can be compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that at least 75%, preferably at least 80%, more preferably at least 90%, and most preferably at least 95% (such as 96%, 97%, 98% or 99%) of the sequence of a given nucleic acid molecule is identical to a given reference sequence. Typically, two polypeptides are considered to be substantially similar if at least 40%, preferably at least 60%, more preferably at least 90%, and most preferably at least 95% (such as 96%, 97%, 98% or 99%) of the amino acids of which the polypeptides are comprised are identical to or represent conservative substitutions of the amino acids of a given reference sequence.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences.

While the above-described nucleic acid molecules can be isolated or purified, alternatively they can be synthesized. Methods of nucleic acid synthesis are known in the art. See, e.g., the references cited herein under "Examples."

The above-described nucleic acid molecules can be used, in whole or in part (i.e., as fragments or primers), to identify and isolate corresponding genes from other organisms for use in the context of the present inventive method using conventional means known in the art. See, for example, the references cited herein under "Examples."

In view of the above, the present invention also provides a vector comprising an above-described isolated or purified nucleic acid molecule. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987) and the references cited herein under "Examples"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λ, SV40, bovine papillomavirus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAM-neo (Clonetech).

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule as described above with a promoter is also within the skill in the art.

Also in view of the above, the present invention provides a cell comprising an isolated or purified nucleic acid molecule or a vector as described above. Examples of suitable cells include, but are not limited to, a human cell, a human cell line, *E. coli*, (e.g., *E. coli* TB-1, TG-2, DH5α, XL-Blue MRF' (Stratagene), SA2821 and Y1090) *B. subtilis, P. aerugenosa, S. cerevisiae*, and *N. crassa*.

The present invention further provides an isolated or purified polypeptide molecule consisting essentially of an amino acid sequence encoding TDC1 or a fragment thereof comprising at least 95 contiguous amino acids, either one of which is optionally glycosylated, amidated, carboxylated, phosphorylated, esterified, N-acylated or converted into an acid addition salt. The isolated or purified polypeptide molecule is preferably obtained from a mammalian source. Even more preferably, the mammalian source is a human. The isolated or purified polypeptide molecule can be encoded by the nucleotide sequence of SEQ ID NO:1 or a fragment thereof comprising at least 285 contiguous nucleotides. Preferably, the isolated or purified polypeptide molecule consists essentially of the amino acid sequence of SEQ ID NO: 2 or a fragment thereof comprising at least 95 contiguous amino acids. More preferably, the fragment comprises at least 100 contiguous amino acids. Still more preferably, the fragment comprises at least 105 contiguous amino acids. Even more preferably, the fragment comprises at least 110 contiguous amino acids. Alternatively, but still preferably, the isolated or purified polypeptide molecule shares 24% or more identity with SEQ ID NO: 2. More preferably, the isolated or purified polypeptide molecule shares 30% or more identity with SEQ ID NO: 2. Still more preferably, the isolated or purified polypeptide molecule shares 45% or more identity with SEQ ID NO: 2. Even more preferably, the isolated or purified polypeptide molecule shares 65% or more identity with SEQ ID NO: 2.

In a further embodiment, the isolated or purified polypeptide molecule can be encoded by the nucleotide sequence of SEQ ID NO: 5 or a fragment thereof comprising at least 285 contiguous nucleotides. Additionally, the isolated or purified polypeptide molecule can consist essentially of the amino acid sequence of SEQ ID NO: 6 or a fragment thereof comprising at least 95 contiguous amino acids. More preferably, the fragment comprises at least 100 contiguous amino acids. Still more preferably, the fragment comprises at least 115 contiguous amino acids. Even more preferably, the fragment comprises at least 130 contiguous amino acids. Alternatively, the isolated or purified polypeptide molecule shares 25% or more identity with SEQ ID NO: 6. More preferably, the isolated or purified polypeptide molecule shares 30% or more identity with SEQ ID NO: 6. Still more preferably, the isolated or purified polypeptide molecule shares 45% or more identity with SEQ ID NO: 6. Even more preferably, the isolated or purified polypeptide molecule shares 65% or more identity with SEQ ID NO: 6.

An isolated or purified polypeptide molecule consisting essentially of an amino acid sequence encoding a variant TDC1 or a fragment thereof can comprise at least 95 contiguous amino acids, which is optionally glycosylated, amidated, carboxylated, phosphorylated, esterified, N-acylated or converted into an acid addition salt. Still preferably, the fragment comprises at least 100 contiguous amino acids. Still more preferably, the fragment comprises at least 105 contiguous amino acids. Even more preferably, the fragment comprises at least 110 contiguous amino acids.

The present invention further provides an isolated or purified polypeptide molecule consisting essentially of an amino acid sequence encoding TDC2 or a fragment thereof comprising at least 71 contiguous amino acids, either one of which is optionally glycosylated, amidated, carboxylated, phosphorylated, esterified, N-acylated or converted into an acid addition salt. The isolated or purified polypeptide molecule is preferably obtained from a mammalian source. Even more preferably, the mammalian source is a human. The isolated or purified polypeptide molecule can be encoded by the nucleotide sequence of SEQ ID NO: 3 or a fragment thereof comprising at least 213 contiguous nucleotides. Preferably, the isolated or purified polypeptide molecule consists essentially of the amino acid sequence of SEQ ID NO: 4 or a fragment thereof comprising at least 71 contiguous amino acids. More preferably, the fragment comprises at least 75 contiguous amino acids. Still preferably, the fragment comprises at least 90 contiguous amino acids. Even more preferably, the fragment comprises at least 105 contiguous amino acids. Alternatively, but still preferably, the isolated or purified polypeptide molecule shares 31% or more identity with SEQ ID NO: 4. More preferably, the isolated or purified polypeptide molecule shares 40% or more identity with SEQ ID NO: 4. Still more preferably, the isolated or purified polypeptide molecule shares 55% or more identity with SEQ ID NO: 4. Even more preferably, the isolated or purified polypeptide molecule shares 75% or more identity with SEQ ID NO: 4.

In a further embodiment, the isolated or purified polypeptide molecule can be encoded by the nucleotide sequence of SEQ ID NO: 7 or a fragment thereof comprising at least 213 contiguous nucleotides. Preferably, the isolated or purified polypeptide molecule consists essentially of the amino acid sequence of SEQ ID NO: 8 or a fragment thereof comprising at least 71 contiguous amino acids. More preferably, the fragment comprises at least 75 contiguous amino acids. Still more preferably, the fragment comprises at least 90 contiguous amino acids. Even more preferably, the fragment comprises at least 105 contiguous amino acids. Alternatively, but still preferably, the isolated or purified polypeptide molecule shares 34% or more identity with SEQ ID NO: 8. More preferably, the isolated or purified polypeptide molecule shares 40% or more identity with SEQ ID NO: 8. Still more preferably, the isolated or purified polypeptide molecule shares 55% or more identity with SEQ ID NO: 8. Even more preferably, the isolated or purified polypeptide molecule shares 75% or more identity with SEQ ID NO: 8.

An isolated or purified polypeptide molecule consisting essentially of an amino acid sequence encoding a variant TDC2 or a fragment thereof can comprise at least 71 contiguous amino acids, which is optionally glycosylated, amidated, carboxylated, phosphorylated, esterified, N-acylated or converted into an acid addition salt. Still preferably, the fragment comprises at least 75 contiguous amino acids. Still more preferably, the fragment comprises at least 90 contiguous amino acids. Even more preferably, the fragment comprises at least 115 contiguous amino acids.

The polypeptide preferably comprises an amino end and a carboxyl end. The polypeptide can comprise D-amino acids, L-amino acids or a mixture of D- and L-amino acids. The D-form of the amino acids, however, is particularly preferred since a polypeptide comprised of D-amino acids is expected to have a greater retention of its biological activity in vivo, given that the D-amino acids are not recognized by naturally occurring proteases.

The polypeptide can be prepared by any of a number of conventional techniques. The polypeptide can be isolated or purified from a naturally occurring source or from a recombinant source. For instance, in the case of recombinant polypeptides, a DNA fragment encoding a desired peptide can be subcloned into an appropriate vector using well-known molecular genetic techniques (see, e.g., Maniatis et al., *Molecular Cloning: A Laboratory Manual,* 2nd ed. (Cold Spring Harbor Laboratory, 1989); and Sambrook et al., Molecular Cloning: A Laboratory Manual, 2nd ed. Cold Spring Harbor Press, Cold Spring Harbor, N.Y., 1989). The fragment can be transcribed and the polypeptide subsequently translated in vitro. Commercially available kits can also be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in the manipulation of nucleic acids. In addition, the polypeptide or fragment thereof can be glycosylated in accordance with methods known in the art.

Alterations of the native amino acid sequence to produce variant polypeptides can be done by a variety of means known to those skilled in the art. For instance, site-specific mutations can be introduced by ligating into an expression vector a synthesized oligonucleotide comprising the modified site. Alternately, oligonucleotide-directed site-specific mutagenesis procedures can be used such as disclosed in Walder et al., *Gene*, 42, 133 (1986); Bauer et al., *Gene*, 37, 73 (1985); Craik, *Biotechniques*, 12–19 (January 1995); and U.S. Pat. Nos. 4,518,584 and 4,737,462.

With respect to the above isolated or purified polypeptides, one of ordinary skill in the art will appreciate that insertions, deletions, inversions and/or substitutions in a nucleotide sequence coding for functional domains of the transductin molecule can lead to a non-functional transductin molecule. Preferably, any variants, as described above, would contain mutations such as insertions, deletions, inversions and/or substitutions in domains which are not critical for transductin activity. For example, as an integral membrane protein, an insertion, inversion, deletion and/or substitution to the transmembrane domain of the transductin molecule may render the molecule unable to insert into the membrane, thus rendering it ineffective as a channel through the cell membrane. Alternatively, the mutation as described above may affect the ability of the channel pore domain to move molecules across the cell membrane. Other domains which are critical for transductin activity can be identified by determining if a mutation(s) to those domains causes a decrease in transductin activity.

Any appropriate expression vector (e.g., as described in Pouwels et al., *Cloning Vectors: A Laboratory Manual* (Elsevior, N.Y.: 1985)) and corresponding suitable host can be employed for production of recombinant polypeptides. Expression hosts include, but are not limited to, bacterial species within the genera *Escherichia, Bacillus, Pseudomonas, Salmonella*, mammalian or insect host cell systems including baculovirus systems (e.g., as described by Luckow et al., *Bio/Technology*, 6, 47 (1988)), and established cell lines such as the COS-7, C127, 3T3, CHO, HeLa, BHK cell line, and the like. The ordinary skilled artisan is, of course, aware that the choice of expression host has ramifications for the type of polypeptide produced. For instance the glycosylation of polypeptides produced in yeast or mammalian cells (e.g., COS-7 cells) will differ from that of polypeptides produced in bacterial cells such as *Escherichia coli*.

Alternately, the polypeptide (including the variant peptides) can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.*, 85, 2149–54 (1963); Barany et al., *Int. J. Peptide Protein Res.*, 30, 705–739 (1987); and U.S. Pat. No. 5,424, 398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means, such as are known to those skilled in the art.

If desired, the polypeptides of the invention (including variant polypeptides) can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create polypeptide derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N- or C-terminus.

Thus, in this regard, the present invention also provides a conjugate comprising an above-described isolated or purified polypeptide molecule or fragment thereof and a targeting moiety. Preferably, the targeting moiety is an antibody or an antigenically reactive fragment thereof. Alternatively, the targeting moiety can be a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). Methods of conjugation are known in the art. In addition, conjugate kits are commercially available.

The present invention also provides a composition comprising a pharmaceutically acceptable carrier and either (i) an above-described isolated or purified nucleic acid molecule or fragment thereof, (ii) an above-described vector, (iii) an above-described polypeptide molecule or fragment thereof, or (iv) an above-described conjugate comprising an above-described isolated or purified polypeptide molecule or fragment thereof and a targeting moiety. Pharmaceutically acceptable carriers are well-known in the art, and are readily available. The choice of carrier will be determined in part by the particular route of administration and whether a nucleic acid molecule or a polypeptide molecule (or conjugate thereof) is being administered. Accordingly, there is a wide variety of suitable formulations for use in the context of the present invention, and the invention expressly provide a pharmaceutical composition that comprises an active agent of the invention and a pharmaceutically acceptable carrier therefor. The following methods and carriers are merely exemplary and are in no way limiting.

Formulations suitable for oral administration can consist of (a) liquid solutions, such as an effective amount of the compound dissolved in diluent, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth. Pastilles can comprise the active ingredient in an inert base, such as gelatin and glycerin, or sucrose and acacia, emulsions, gels, and the like containing, in addition to the active ingredient, such excipients/carriers as are known in the art.

An active agent of the present invention, either alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, active agents of the present invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate. Further suitable formulations are found in *Remington's Pharmaceutical Sciences*, 17th ed., (Mack Publishing Company, Philadelphia, Pa.: 1985), and methods of drug delivery are reviewed in, for example, Langer, *Science,* 249, 1527–1533 (1990).

A targeting moiety also can be used in the contact of a cell with an above-described isolated or purified nucleic acid molecule. In this regard, any molecule that can be linked with the therapeutic nucleic acid directly or indirectly, such as through a suitable delivery vehicle, such that the targeting moiety binds to a cell-surface receptor, can be used. The targeting moiety can bind to a cell through a receptor, a substrate, an antigenic determinant or another binding site on the surface of the cell. Examples of a targeting moiety include an antibody (i.e., a polyclonal or a monoclonal antibody), an immunologically reactive fragment of an antibody, an engineered immunoprotein and the like, a protein (target is receptor, as substrate, or regulatory site on DNA or RNA), a polypeptide (target is receptor), a peptide (target is receptor), a nucleic acid, which is DNA or RNA (i.e., single-stranded or double-stranded, synthetic or isolated and purified from nature; target is complementary nucleic acid), a steroid (target is steroid receptor), and the like.

Analogs of targeting moieties that retain the ability to bind to a defined target also can be used. In addition, synthetic targeting moieties can be designed, such as to fit a particular epitope. Alternatively, the therapeutic nucleic acid can be encapsulated in a liposome comprising on its surface the targeting moiety.

The targeting moiety includes any linking group that can be used to join a targeting moiety to, in the context of the present invention, an above-described nucleic acid molecule. It will be evident to one skilled in the art that a variety of linking groups, including bifunctional reagents, can be used. The targeting moiety can be linked to the therapeutic nucleic acid by covalent or non-covalent bonding. If bonding is non-covalent, the conjugation can be through hydrogen bonding, ionic bonding, hydrophobic or van der Waals interactions, or any other appropriate type of binding.

Further provided by the present invention is a cell line that produces a monoclonal antibody that is specific for an above-described isolated or purified polypeptide molecule. Methods of making such cell lines are known in the art (see, e.g., the references cited herein under "Examples."). Preferably, the cells from which the cell line is created are pluripotent stem cells. Even more preferably, the cells are totipotent stem cells. Thus, the present invention also provides the monoclonal antibody produced by the cell line.

The invention further provides methods for detecting hearing loss or a predisposition to hearing loss in an animal. In one embodiment, the method comprises detecting at least one mutation such as 1714G→A (D572N), 100C→T (R34X), 1534C→T (R512X), 295 del A (frameshift and premature termination), 1960 A→G (M654V), IVS3_IVS5del27 kb, IVS13+1G→A, or IVS10-8T→A, in a gene encoding TDC1 in a test sample comprising a nucleic acid comprising the TDC1 gene, and/or a polymorphism thereof, obtained from the animal, wherein the at least one mutation is indicative of hearing loss or a predisposition to hearing loss in the animal. In another embodiment, the method comprises detecting at least one mutation in a gene encoding TDC2 in a test sample comprising a nucleic acid comprising the TDC2 gene, and/or a polymorphism thereof, obtained from the animal, wherein the at least one mutation is indicative of hearing loss or a predisposition to hearing loss in the animal. The hearing loss can be hereditary, and can further be sensorineural hearing loss. The method can further be used to treat nonsyndromic autosomal-dominant hearing loss. The hearing loss can also be aminoglycoside induced. Furthermore, the hearing loss can be linked to DFNA 36. The method also has application wherein the at least one mutation compromises the ability of the TDC1/TDC2 gene product to form a component of a hair cell of the inner ear of the animal. The component of the hair cell can be all or some of an ion transduction channel of the hair cell of the inner ear of the animal. Alternatively, the at least one mutation can compromise the mechanosensory activity of the TDC1/TDC2 gene product.

The at least one mutation (e.g., at least two mutations, at least three mutations, at least four mutations, at least five mutations, or even at least ten mutations) in a gene encoding transductin is defined herein as any one or more mutations in the gene encoding transductin which is/are indicative of hearing loss or a predisposition to hearing loss in an animal. The at least one mutation can be, for example, any frameshift mutations, missense mutations and/or nonsense mutations, arising from any insertion, duplication, deletion, inversion, and/or substitution in a gene encoding transductin. The at least one mutation can cause transcriptional, post-transcriptional, translational, and/or post-translational processing errors, e.g., a translation error wherein translation begins at a codon encoding a methionine other than the first methionine of the transductin gene (e.g., a codon encoding the third methionine of the transductin gene). Moreover, the at least one mutation in the transductin gene can cause one or more splicing errors (i.e., splicing mutations), such that a mutant transductin gene is produced. Alternatively, or in addition to, the at least one mutation in the transductin gene can be a mutation that causes transcriptional, post-transcriptional, translational, and/or post-translational processing of the transductin gene to stop prematurely, thereby leading to the expression of a truncated form of transductin. The at least one mutation can also cause a decreased efficiency of transcriptional, post-transcriptional, translational, and/or post-translational processing of the transductin gene product. Moreover, the at least one mutation in the transductin gene can be associated with a compromised ability of the transductin gene product to function normally, as compared to wild-type transductin.

The at least one mutation in the transductin gene can be detected at one or more nucleic acid positions of the transductin gene, e.g., within any coding region, and/or regulatory region of the transductin gene. The at least one mutation in the transductin gene is indicative of hearing loss or a predisposition to hearing loss in the animal if, for example, the at least one mutation compromises the transmembrane domain allowing the transductin molecule to traverse the cell membrane. The at least one mutation in the transductin gene also is indicative of hearing loss or a predisposition to hearing loss in an animal if it compromises the ability of the transductin molecule from associating with other such molecules to form an ion channel. Moreover, the at least one mutation in the transductin gene is indicative of hearing loss or a predisposition to hearing loss in an animal if the at least one mutation compromises the ability of the transductin gene product to become activated, as compared to wild-type transductin; or compromises the ability of the channel complex to channel ions across a cell membrane.

The transductin gene in a test sample obtained from an animal can be amplified using any suitable amplification method known in the art, e.g., polymerase chain reaction (PCR); reverse transcriptase PCR (RT-PCR); ligase chain reaction (LCR) (disclosed in U.S. Pat. No. 4,883,750); isothermal amplification (disclosed in Walker et al., *Proc. Natl. Acad. Sci. USA* 89: 392–396 (1992)); strand displacement amplification (SDA); and repair chain reaction (RCR). Target-specific sequences also can be detected using a cyclic probe reaction (CPR). Moreover, alternative methods for reverse transcription are described in WO 90/07641.

Any primer sequences can be used in the amplification process, as long as the primer sequences are hybridizable to nucleic acids encoding a wild-type transductin gene, a mutant transductin gene, and/or functional sequence analogs thereof. For example, M13-tailed primers can be used in the amplification process (see Table 1).

The nucleic acid used as a template for amplification can be isolated from a test sample using any standard methodology (Sambrook et al., Molecular Cloning: A Laboratory Manual, $2^{nd}$ Ed., Cold Spring Harbor Press, Cold Spring Harbor, N.Y., 1989). Alternatively, or in addition to, chromatographic techniques can be employed to effect separation. It will be understood that there are many kinds of chromatography which can be used in the context of the method, e.g., adsorption, partition, ion-exchange and molecular sieve, and many specialized techniques for using them including column, paper, thin-layer and gas chromatography (Freifelder, *Physical Biochemistry Applications to Biochemistry and Molecular Biology*, $2^{nd}$ Ed., Wm. Freeman and Co., New York, N.Y. (1982)).

Amplification products must be visualized in order to confirm amplification of the transductin gene. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation. In one embodiment, visualization is achieved indirectly. Following separation of amplification products, a labeled, nucleic acid probe is brought into contact with and allowed to hybridize with the amplified transductin gene sequence. The probe preferably is conjugated to a chromophore, but may be radiolabeled. In another embodiment, the probe is conjugated to a binding partner, such as an antibody or biotin, where the other member of the binding pair carries a detectable moiety (i.e., a label). One example of the foregoing is described in U.S. Pat. No. 5,279,721, which discloses an apparatus and method for the automated electrophoresis and transfer of nucleic acids.

When hybridization is employed, preferably, the hybridization is done under high stringency conditions. By "high stringency conditions" is meant that the probe specifically hybridizes to a target sequence in an amount that is detectably stronger than non-specific hybridization. High stringency conditions, then, are conditions that distinguish a polynucleotide with an exact complementary sequence, or one containing only a few scattered mismatches from a random sequence that happened to have a few small regions (e.g., 3–10 bases) that matched the probe. Such small regions of complementarity are more easily melted than a full-length complement of 14–17 or more bases, and moderate stringency hybridization makes them easily distinguishable. Relatively high stringency conditions include, for example, low salt and/or high temperature conditions, such as provided by about 0.02–0.1 M NaCl or the equivalent, at temperatures of about 50–70° C. Such relatively high stringency conditions tolerate little, if any, mismatch between the probe and the template or target strand, and are particularly suitable for detecting expression of specific transductins. It is generally appreciated that conditions can be rendered more stringent by the addition of increasing amounts of formamide.

The at least one mutation can be detected by sequencing the transductin gene, and comparing the sequence to the wild-type sequence. Alternatively, the at least one mutation may be detected by Southern blot hybridization, a method well known in the art. Yet another alternative is by allele-specific PCR amplification of genomic DNA.

In addition to the above, the invention provides a method of determining the level of nucleic acid comprising the wild-type TDC1 gene and/or a mutant TDC1 gene in a test sample comprising a nucleic acid comprising the wild-type TDC1 gene and/or a mutant TDC1 gene obtained from an animal. The method comprises assaying the test sample for the level of nucleic acid comprising the wild-type TDC1 gene and/or a mutant TDC1 gene, wherein a decrease in the level of nucleic acid comprising the wild-type TDC1 gene and/or an increase in the level of nucleic acid comprising a mutant TDC1 gene in the test sample as compared to a control sample is indicative of hearing loss (e.g., hearing loss) or a predisposition to hearing loss in the animal.

In addition to the above, the invention provides a method of determining the level of nucleic acid comprising the wild-type TDC2 gene and/or a mutant TDC2 gene in a test sample comprising a nucleic acid comprising the wild-type TDC2 gene and/or a mutant TDC2 gene obtained from an animal. The method comprises assaying the test sample for the level of nucleic acid comprising the wild-type TDC2 gene and/or a mutant TDC2 gene, wherein a decrease in the level of nucleic acid comprising the wild-type TDC2 gene and/or an increase in the level of nucleic acid comprising a mutant TDC2 gene in the test sample as compared to a control sample is indicative of hearing loss (e.g., hearing loss) or a predisposition to hearing loss in the animal.

A wild-type transductin gene is defined herein is any transductin gene that encodes an transductin gene product that has (i.e., possesses) cation channel capabilities across a cell membrane. A mutant transductin gene is defined herein as any transductin gene that encodes a transductin gene product which has a compromised ability (e.g., little or no ability) to channel cations across a cell membrane, as compared to wild-type transductin.

The level of a wild-type transductin gene and/or a mutant transductin gene in a test sample obtained from an animal is defined herein as the quantity of nucleic acid comprising a wild-type transductin gene and/or the quantity of nucleic acid comprising a mutant transductin gene in the test sample. "Decreased" and "increased" levels of the wild-type transductin gene and/or a mutant transductin gene are determined by a comparison of the level of wild-type and/or mutant transductin genes present in a test sample obtained from an animal to any suitable control test sample. Suitable control test samples include, for example, a test sample obtained from the same animal at a different point in time and a test sample obtained from a different animal of the same species.

Various assays can be used to measure the presence and/or level of nucleic acid (i.e., DNA or RNA) comprising a wild-type transductin gene and/or a mutant transductin gene present in a test sample obtained from an animal. For example, assays including PCR and microarray analysis can be used to detect the presence and/or absence of the wild-type transductin gene and/or a mutant transductin gene, as described, for example, in U.S. Pat. Nos. 6,197,506 and 6,040,138. Moreover, it is understood that the type of assay used depends on whether the nucleic acid of interest being assayed is DNA or RNA. Assays for determining the level of DNA comprising a wild-type transductin gene and/or a mutant transductin gene in a test sample include, for example, Southern hybridization (i.e., a Southern blot), in situ hybridization and microarray analysis. Assays for determining the level of RNA (e.g., mRNA) comprising a wild-type transductin gene and/or a mutant transductin gene in a test sample include, for example, Northern hybridization (i.e., a Northern blot), in situ hybridization and microarray analysis.

It is also understood that a nucleic acid sequence that specifically binds to, or associates with, a nucleic acid comprising a gene encoding transductin, whether DNA or RNA, can be attached to a label for determining hybridization. A wide variety of appropriate labels are known in the art, including, for example, fluorescent, radioactive, and enzymatic labels, as well as ligands (e.g., avidin/biotin), which are capable of being detected. Preferably, a fluorescent label or an enzyme tag, such as urease, alkaline phosphatase or peroxidase, is used instead of a radioactive or other environmentally undesirable label. In the case of enzyme tags, colorimetric indicator substrates are known which can be employed to provide a detection system that is visible spectrophotometrically, or even visible to the human eye to identify specific hybridization with complementary transductin nucleic acid-containing samples.

The invention also provides for the use of the method in prognosticating hearing loss (e.g., hearing loss) in an animal. The method comprises determining the level of nucleic acid comprising the wild-type TDC1/TDC2 gene and/or a mutant TDC1/TDC2 gene in a test sample comprising a nucleic acid comprising the wild-type TDC1/TDC2 gene and/or a mutant TDC1/TDC2 gene obtained from the animal, and comparing the level of nucleic acid comprising the wild-type TDC1/TDC2 gene and/or a mutant TDC1/TDC2 gene in the test sample to the level of nucleic acid comprising the wild-type TDC1/TDC2 gene and/or a mutant TDC1/TDC2 gene, respectively, in another test sample obtained from the animal over time, wherein a decrease in the level of nucleic acid comprising the wild-type TDC1/TDC2 gene and/or an increase in the level of nucleic acid comprising a mutant TDC1/TDC2 gene is indicative of an unfavorable prognosis, an increase in the level of the nucleic acid comprising the wild-type TDC1/TDC2 gene and/or a decrease in the level of the nucleic acid comprising a mutant TDC1/TDC2 gene is indicative of a favorable prognosis, and no change in the level of nucleic acid comprising the wild-type TDC1/TDC2 gene and/or a mutant TDC1/TDC2 gene is indicative of no change in the hearing loss.

The invention also provides for the use of the method in assessing the efficacy of treatment of hearing loss in the animal with a given anti-hearing loss agent. The method comprises comparing the level of nucleic acid comprising the wild-type TDC1/TDC2 gene and/or a mutant TDC1/TDC2 gene in the test sample to the level of nucleic acid comprising the wild-type TDC1/TDC2 gene and/or a mutant TDC1/TDC2 gene, respectively, in another test sample obtained from the animal over time, wherein a decrease in the level of nucleic acid comprising the wild-type TDC1/TDC2 gene and/or an increase in the level of nucleic acid comprising a mutant TDC1/TDC2 gene is indicative of the anti-hearing loss agent being effective, an increase in the level of the nucleic acid comprising the wild-type TDC1/TDC2 gene and/or a decrease in the level of the nucleic acid comprising a mutant TDC1/TDC2 gene is indicative of the anti-hearing loss agent being ineffective, and no change in the level of nucleic acid comprising the wild-type TDC1/TDC2 gene and/or a mutant TDC1/TDC2 gene is indicative of no change in the hearing loss due to treatment with the anti-hearing loss agent.

A mutant transductin gene product also can be detected in a test sample obtained from an animal and is indicative of hearing loss or a predisposition to hearing loss in the animal. Accordingly, the present invention further provides a method for detecting hearing loss or a predisposition to hearing loss in an animal comprising detecting a mutant transductin in a test sample comprising protein comprising transductin obtained from the animal, wherein the presence of a mutant transductin in the test sample is indicative of hearing loss or a predisposition to hearing loss in the animal. Examples of such mutations, which are indicative of hearing loss or a predisposition to hearing loss, have been described above. Thus, the method comprises detecting a mutant TDC1/TDC2 in a test sample comprising protein comprising TDC1/TDC2 obtained from the animal, wherein the presence of a mutant TDC1/TDC2 in the sample is indicative of hearing loss, or a predisposition to hearing loss in the animal. The hearing loss can be hereditary, sensorineural hearing loss, nonsyndromic autosomal-dominant, and/or DFNA 36-linked hearing loss. The ability of the mutant TDC1/TDC2 to form a component of a hair cell of the inner ear of the animal can be compromised. The ability of the mutant TDC1/TDC2 to form all or some of an on transduction channel of the hair cell of the inner ear of the animal can be compromised. The mechanosensory activity of the mutant TDC1/TDC2 can also be compromised.

The levels of wild-type TDC1/TDC2 and/or a mutant TDC1/TDC2 also can be determined. Accordingly, the invention also provides a method of determining the level of wild-type TDC1/TDC2 and/or a mutant TDC1/TDC2 in a test sample comprising protein comprising wild-type TDC1/TDC2 and/or a mutant TDC1/TDC2 obtained from an animal. The method comprises assaying the test sample for the level of wild-type TDC1/TDC2 and/or a mutant TDC1/TDC2, wherein a decrease in the level of wild-type TDC1/TDC2 and/or an increase in the level of a mutant TDC1/TDC2 in the test sample as compared to a control sample (as described previously) is indicative of hearing loss or a predisposition to hearing loss in the animal.

Various assays (i.e., immunobinding assays) are contemplated for detecting and/or measuring the quantity of wild-type transductin and/or a mutant transductin in a test sample obtained from an animal. For example, separate and distinct antibodies can be prepared and employed to detect wild-type transductin and a mutant transductin, respectively. Alternatively, wild-type transductin and a mutant transductin can be utilized to detect antibodies having reactivity therewith. The steps of various useful immunodetection assays have been described, for example, in Nakamura et al., *Handbook of Experimental Immunology* ($4^{th}$ Ed)., Vol. 1, Chapter 27, Blackwell Scientific Publ., Oxford (1987); Nakamura et al., *Enzyme Immunoassays: Heterogenous and Homogenous Systems*, Chapter 27 (1987). Suitable immunoassays include, for example, Western hybridization (i.e., Western blots), immunoaffinity purification, immunoaffinity detection, enzyme-linked immunosorbent assay (e.g., an ELISA), and radioimmunoassay. Moreover, a microarray can be used to detect and/or measure the levels of wild-type transductin and/or a mutant transductin in a test sample obtained from an animal.

In general, the immunobinding assays involve obtaining a test sample suspected of containing a protein, peptide, polypeptide, and/or antibody corresponding to wild-type transductin and/or a mutant transductin, and contacting the test sample with one or more antibodies under conditions effective to allow the formation of immunocomplexes. It is suitable, for example, to contact concurrently, or sequentially, a test sample obtained from an animal with an antibody that is specific to wild-type transductin and with an antibody that is specific to a mutant transductin.

Any suitable antibody can be used in conjunction with the present invention such that the antibody is specific for wild-type transductin. Likewise, any suitable antibody can be used in conjunction with the present invention such that the antibody is specific for a mutant transductin. In particular, suitable antibodies recognize and interact with (i.e., bind to) one or more portions of wild-type transductin and with one or more portions of a mutant transductin. Moreover, suitable antibodies include antibodies that recognize and interact with other antibodies present in a test sample that bind to wild-type transductin. Likewise, suitable antibodies include antibodies that recognize and interact with other antibodies present in a test sample that bind to a mutant transductin. Antibodies for use in the present inventive methods can be produced by any known technique, e.g., as described in Antibodies: A Laboratory Manual, Cold Spring Harbor Laboratory (1988).

Contacting a test sample comprising a protein comprising wild-type transductin and/or a mutant transductin with an antibody or antibodies that recognize wild-type transductin and/or a mutant transductin under conditions effective, and for a period of time sufficient, to allow for formation of immune complexes (primary immune complexes) is generally a matter of adding the antibody to the test sample and incubating the mixture for a period of time long enough for the antibodies to form immune complexes with wild-type transductin and/or a mutant transductin. Detection of immunocomplex formations can be achieved through the application of numerous techniques which are well-known in the art. These detection methods are generally based upon the detection of a label or marker, such as any radioactive, fluorescent, biological a enzymatic labels of standard use in the art, as described, for example, in U.S. Pat. Nos. 3,817,837, 3,850,752, 3,939,350, 3,996,345, 4,277,437, 4,275,149 and 4,366,241. Of course, additional advantages can be realized by using a secondary binding ligand, such as a second antibody or a biotin/avidin ligand binding arrangement, as is known in the art.

The antibody or antibodies which is/are used in the context of the present invention can, themselves, be linked to a detectable label. Such a detectable label allows for the presence of, or the amount of, the primary immune complexes to be determined. Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

The invention also provides for the use of the method in prognosticating hearing loss in an animal. The method comprises comparing the level of wild-type TDC1/TDC2 and/or a mutant TDC1/TDC2 in the test sample to the level of wild-type TDC1/TDC2 and/or a mutant TDC1/TDC2, respectively, in another test sample obtained from the animal over time, wherein a decrease in the level of wild-type TDC1/TDC2 and/or an increase in the level of a mutant TDC1/TDC2 is indicative of an unfavorable prognosis, an increase in the level of the wild-type TDC1/TDC2 and/or a decrease in the level of a mutant TDC1/TDC2 is indicative of a favorable prognosis, and no change in the level of the wild-type TDC1/TDC2 and/or a mutant TDC1/TDC2 gene is indicative of no change in the hearing loss.

The invention also provides for the use of the method in assessing the efficacy of treatment of hearing loss in an animal. The method comprises comparing the level of wild-type TDC1/TDC2 and/or a mutant TDC1/TDC2 in the test sample to the level of wild-type TDC1/TDC2 and/or a mutant TDC1/TDC2, respectively, in another test sample obtained from the animal over time, wherein a decrease in the level of the wild-type TDC1/TDC2 and/or an increase in the level of a mutant TDC1/TDC2 is indicative of the anti-hearing loss agent being effective, an increase in the level of the wild-type TDC1/TDC2 and/or a decrease in the level of a mutant TDC1/TDC2 is indicative of the anti-hearing loss agent being ineffective, and no change in the level of the wild-type TDC1/TDC2 and/or a mutant TDC1/

TDC2 is indicative of no change in the hearing loss due to treatment with the anti-hearing loss agent.

The invention also provides a method of treating an animal prophylactically or therapeutically for hearing loss (e.g., hearing loss), wherein the hearing loss is due to a complete or partial loss of wild-type TDC1/TDC2, which method comprises providing TDC1/TDC2 to the animal, whereupon the animal is treated prophylactically or therapeutically for hearing loss. Use of the terms "prophylactically," "prophylaxis," and derivatives of these terms is not meant to be limited to absolute prevention of hearing loss, but also less than 100% prevention of hearing loss. The ordinarily skilled artisan will appreciate that a less than 100% prevention of hearing loss may still be beneficial to an animal, and thus contemplated to be within the scope of the present invention. The hearing loss can be hereditary, sensorineural hearing loss, nonsyndromic autosomal-dominant, and/or DFNA 36-linked hearing loss. The ability of the mutant TDC1/TDC2 to form a component of a hair cell of the inner ear of the animal can be compromised. The ability of the mutant TDC1/TDC2 to form all or some of an on transduction channel of the hair cell of the inner ear of the animal can be compromised. The mechanosensory activity of the mutant TDC1/TDC2 also can be compromised.

Any suitable method can be used for administering or providing transductin to an animal, wherein the transductin enters the nucleus and/or cytoplasm of one or more hearing loss cells (e.g., one or more hearing loss cells) of the animal and functions within the cell(s) in a manner which is typical of wild-type transductin. For example, transductin can be provided to the animal by administering to the animal the wild-type transductin protein, or a portion thereof (e.g., two or more different forms of wild-type transductin). Moreover, transductin can be provided to an animal through administration of a fusion protein comprising wild-type transductin, or a portion thereof, operably linked to one or more moieties of interest (e.g., two or more, three or more, four or more, or five or more therapeutic moieties, such as anti-hearing loss agents, and/or any compounds which stimulate transductin). In another embodiment, transductin is provided to an animal through administration of a nucleic acid encoding and expressing wild-type transductin, or a portion thereof. Moreover, transductin can be provided to an animal through administration of a nucleic acid encoding and expressing a fusion protein comprising wild-type transductin, or a portion thereof, operably linked to one or more moieties of interest. The administered nucleic acid can be in any suitable form. For example, the administered nucleic acid can be naked DNA or RNA. Moreover, the administered nucleic acid can be part of any suitable vector or vector system. Suitable vectors for use in the method include, for example, plasmid vectors, retroviral vectors, adenoviral vectors, adeno-associated viral vectors, vaccinia virus, sindbis virus, cytomegalovirus, herpes simplex virus, defective hepatitis B viruses, and any other vector or vector system known in the art. Fusion proteins and nucleic acids encoding and expressing fusion proteins can be produced using any standard methods of recombinant production and synthesis known in the art, as described, for example, in Sambrook et al., *Molecular Cloning: A Laboratory Manual*, $2^{nd}$ Ed., Cold Spring Harbor Press, Cold Spring Harbor, N.Y., 1989.

In view of the above, also provided is a composition. The composition comprises (i) a pharmaceutically acceptable carrier and (ii) transductin or a portion thereof; a fusion protein comprising transductin or a portion thereof, operably linked to one or more moieties of interest; a nucleic acid encoding and expressing transductin or a portion thereof; and/or a nucleic acid encoding and expressing a fusion protein comprising transductin or a portion thereof, operably linked to one or more moieties of interest.

The carrier can be any suitable carrier. Preferably, the carrier is a pharmaceutically acceptable carrier. With respect to compositions, the carrier can be any of those conventionally used and is limited only by chemico-physical considerations, such as solubility and lack of reactivity with transductin, and by the route of administration. It will be appreciated by one of skill in the art that, in addition to the above-described composition, the compositions of the present inventive methods can be formulated as inclusion complexes, such as cyclodextrin inclusion complexes, or liposomes. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to transductin and one which has no detrimental side effects or toxicity under the conditions of use.

As is understood in the art, the choice of carrier is dependent on several factors, e.g., the type of hearing loss being treated and the route of administration of the composition. Such a choice of carrier for use in the composition of the present invention is well within the ordinary skill in the art. Accordingly, there are a variety of suitable formulations of the composition of the present invention. Such formulations include but, are not limited to, oral, aerosol, parenteral, subcutaneous, intravenous, intramuscular, interperitoneal, rectal, and vaginal formulations.

One skilled in the art will appreciate that suitable methods of administering a composition of the invention to an animal, in particular a human, are available, and, although more than one route can be used to administer a particular compound, a particular route can provide a more immediate and more effective reaction than another route.

Desirably, gene replacement therapy would be employed to treat therapeutically hereditary deafness in a mammal resulting from a mutation or deletion of TDC1 and/or TDC2. Methods of constructing vectors encoding therapeutic genes are known to one of ordinary skill in the art. Such constructs include viral vectors, preferably adenoviral or adeno-associated viral vectors, naked DNA, plasmid vector, and other genetic constructs. The vectors can be delivered by any method known in the art. Ideally, these vectors would be delivered to the animal transtympanically.

The dose administered to an animal, in particular a human, should be sufficient to treat the hearing loss prophylactically or therapeutically. One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, a composition is initially administered in smaller dosages, which are less than the optimum dose of the composition. Thereafter, the dosage is increased by small increments until the optimum effect under the circumstances is reached.

Also provided is a method of identifying one or more agent(s) which interact with a mechanotransduction channel of a cell of an animal. This method comprises administering one or more agent(s) to the mechanotransduction channel and assaying the mechanotransduction activity of the mechanotransduction channel, wherein an increase or decrease in the mechanotransduction activity of the mechanotransduction channel is indicative of an interaction between one or more agents and the mechanotransduction channel of the cell of the animal. Preferably, the cell used in the present method would be a hair cell of the inner ear of the animal.

The activity of the mechanotransduction can be measured by techniques known to one of ordinary skill in the art. For example, the channel of ions across a cell membrane to create a electropotential can be measured as generally described by Corey et al., Ionic basis of the receptor potential in a vertebrate hair cell, *Nature* 281: 675–77 (1979), and Hudspeth et al., Sensitivity, polarity, and conductance change in response of vertebrate hair cells to controlled mechanical stimuli, *Proc. Natl. Acad. Sci. USA* 74(6): 2407–11 (1977).

Further provided is a method of identifying one or more agent(s) which interact with a TDC1 gene and/or a TDC2 gene in a cell, comprising administering one or more agents to the cell comprising the TDC1 gene and/or the TDC2 gene and assaying the expression level of the TDC1 gene and/or the TDC2 gene by the cell as described herein, supra, wherein an increase or decrease in the expression level of the TDC1 gene and/or the TDC2 gene, as the terms have been described, supra, is indicative of an interaction between one or more agents and the TDC1 gene and/or the TDC2 gene in the cell.

The ordinarily skilled artisan will recognize that several methods of assaying the expression level of the TDC1 gene and/or the TDC2 gene exist. For example, mRNA can be quantified by a Northern blot analysis using a polynucleotide synthesized to hybridize to mRNA encoding TDC1 and/or TDC2. The polynucleotide can be attached to a probe, or can contain a radioisotope to facilitate detection of specific hybridization of mRNA encoding TDC1 and/or TDC2. Alternatively, the level of expression of the TDC1 gene and/or the TDC2 gene can also be assayed by quantifying the TDC1 and/or TDC2 polypeptide produced by the cell. For example, the cells to which the one or more agents have been administered can be contacted with a monoclonal antibody specific to TDC1 or TDC2. Antibody assays for protein are also well-known in the art as described, supra.

While the present invention is described above in the context of hearing loss, it is possible that the present invention has application in the context of balance. Indeed, the inner ear is known to comprise two systems: the auditory system, which is mainly used for audition, and the vestibular system, which functions in maintaining balance and equilibrium of the body. It has been described herein that when the auditory system (i.e., the cochlea) expresses mutant forms of either TDC1 and/or TDC2, hearing loss results. It is possible, therefore, that the vestibular system, which is responsible for linear and angular acceleration (i.e., balance), can express mutant forms of these genes as well; however, since the vestibular system controls balance as opposed to audition, it is likely that mutations and/or low expression levels of these genes in the vestibular system would result in abnormal balance or even a complete loss of balance. Thus, the methods of the invention, as they relate to TDC1 and TDC2, can be carried out with respect to hearing loss and, possibly, abnormal balance or a predisposition to abnormal balance as well.

EXAMPLE

The following example further illustrates the invention but, of course, should not be construed as in any way limiting its scope.

The following references, to the extent that they provide exemplary procedural or other details supplementary to those set forth herein, are specifically incorporated herein by reference:

Birren et al., *Genome Analysis: A Laboratory Manual Series, Volume 1, Analyzing DNA*, Cold Spring Harbor Laboratory Press, Cold Spring Harbor, N.Y. (1997), Birren et al., *Genome Analysis: A Laboratory Manual Series, Volume 2, Detecting Genes*, Cold Spring Harbor Laboratory Press, Cold Spring Harbor, N.Y. (1998), Birren et al., *Genome Analysis: A Laboratory Manual Series, Volume 3, Cloning Systems*, Cold Spring Harbor Laboratory Press, Cold Spring Harbor, N.Y. (1999), Birren et al., *Genome Analysis: A Laboratory Manual Series, Volume 4, Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), and Sambrook et al., *Molecular Cloning: A Laboratory Manual*, 2nd edition, Cold Spring Harbor Laboratory Press, Cold Spring Harbor, N.Y. (1989).

Mouse and human cochlear cells were lysed, and mRNA transcripts were purified from the cell lysate. Methods of cell lysis and subsequent mRNA purification are well-known in the art. The Human Genome Project database was analyzed for the sequences in the human genome that correlated highly with hearing loss in linkage studies. DNA primers were constructed from this information using techniques known in the art. These primers were employed in reverse transcriptase-polymerase chain reaction (RT-PCR) and 5'- and 3'-rapid amplification of cDNA ends (RACE) on the purified mRNA from cochlear cell lysates. Both methods are also well-known in the art. The resulting cDNA molecules were sequenced and identified as TDC1 and TDC2.

All of the references cited herein are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. An isolated or purified nucleic acid molecule comprising SEQ ID NO: 3.

2. An isolated or purified nucleic acid molecule comprising a nucleotide sequence that encodes the amino acid sequence of SEQ ID NO: 4.

3. An isolated or purified nucleic acid molecule comprising a nucleotide sequence that is complementary to an isolated or purified nucleic acid molecule comprising SEQ ID NO: 3.

4. An isolated or purified nucleic acid molecule comprising a nucleotide sequence that is complementary to a nucleotide sequence encoding the amino acid sequence of SEQ ID NO: 4.

5. A vector comprising the isolated or purified nucleic acid molecule of claim 1.

6. A vector comprising the isolated or purified nucleic acid molecule of claim 3.

7. A composition comprising the isolated or purified nucleic acid molecule of claim 1 and a pharmaceutically acceptable carrier.

8. A composition comprising the isolated or purified nucleic acid molecule of claim 3 and a pharmaceutically acceptable carrier.

9. An isolated cell comprising the vector of claim 5.

10. An isolated cell comprising the vector of claim 6.

11. A method of detecting hearing loss or a predisposition to hearing loss in an animal, which method comprises detecting at least one mutation in a gene encoding TDC2 in a test sample comprising a nucleic acid comprising the TDC2 gene obtained from the animal, wherein a wild-type TDC2 gene encodes SEQ ID NO: 4, and the at least one mutation is indicative of hearing loss or a predisposition to hearing loss in the animal.

12. A method of determining the level of nucleic acid comprising the wild-type TDC2 gene and/or a mutant TDC2 gene in a test sample comprising a nucleic acid comprising the wild-type TDC2 gene and/or a mutant TDC2 gene obtained from an animal, which method comprises assaying the test sample for the level of nucleic acid comprising the wild-type TDC2 gene and/or a mutant TDC2 gene, wherein the wild-type TDC2 gene encodes SEQ ID NO: 4, and a decrease in the level of nucleic acid comprising the wild-type TDC2 gene and/or an increase in the level of nucleic acid comprising a mutant TDC2 gene in the test sample as compared to a control sample is indicative of hearing loss or a predisposition to hearing loss in the animal.

13. The method of claim 12, wherein the method is used for prognosticating hearing loss in the animal, which method further comprises comparing the level of nucleic acid comprising the wild-type TDC2 gene and/or a mutant TDC2 gene in the test sample to the level of nucleic acid comprising the wild-type TDC2 gene and/or a mutant TDC2 gene, respectively, in another test sample obtained from the animal over time, wherein the wild-type TDC2 gene encodes SEQ ID NO: 4, and wherein a decrease in the level of nucleic acid comprising the wild-type TDC2 gene and/or an increase in the level of nucleic acid comprising a mutant TDC2 gene is indicative of an unfavorable prognosis, an increase in the level of the nucleic acid comprising the wild-type TDC2 gene and/or a decrease in the level of the nucleic acid comprising a mutant TDC2 gene is indicative of a favorable prognosis, and no change in the level of nucleic acid comprising the wild-type TDC2 gene and/or a mutant TDC2 gene is indicative of no change in the hearing loss.

14. The method of claim 12, wherein the method is used for assessing the efficacy of treatment of hearing loss in the animal with a given anti-hearing loss agent, which method further comprises comparing the level of nucleic acid comprising the wild-type TDC2 gene and/or a mutant TDC2 gene in the test sample to the level of nucleic acid comprising the wild-type TDC2 gene and/or a mutant TDC2 gene, respectively, in another test sample obtained from the animal over time, wherein the wild-type TDC2 gene encodes SEQ ID NO: 4, and wherein a decrease in the level of nucleic acid comprising the wild-type TDC2 gene and/or an increase in the level of nucleic acid comprising a mutant TDC2 gene is indicative of the anti-hearing loss agent being effective, an increase in the level of the nucleic acid comprising the wild-type TDC2 gene and/or a decrease in the level of the nucleic acid comprising a mutant TDC2 gene is indicative of the anti-hearing loss agent being ineffective, and no change in the level of nucleic acid comprising the wild-type TDC2 gene and/or a mutant TDC2 gene is indicative of no change in the hearing loss due to treatment with the anti-hearing loss agent.

15. A vector comprising the isolated or purified nucleic acid molecule of claim 2.

16. A vector comprising the isolated or purified nucleic acid molecule of claim 4.

17. A composition comprising the isolated or purified nucleic acid molecule of claim 2 and a pharmaceutically acceptable carrier.

18. A composition comprising the isolated or purified nucleic acid molecule of claim 4 and a pharmaceutically acceptable carrier.

19. A composition comprising the vector of claim 5 and a pharmaceutically acceptable carrier.

20. A composition comprising the vector of claim 6 and a pharmaceutically acceptable carrier.

21. A composition comprising the vector of claim 15 and a pharmaceutically acceptable carrier.

22. A composition comprising the vector of claim 16 and a pharmaceutically acceptable carrier.

23. An isolated cell comprising the isolated or purified nucleic acid molecule of claim 1.

24. An isolated cell comprising the isolated or purified nucleic acid molecule of claim 2.

25. An isolated cell comprising the isolated or purified nucleic acid molecule of claim 3.

26. An isolated cell comprising the isolated or purified nucleic acid molecule of claim 4.

27. An isolated cell comprising the vector of claim 15.

28. An isolated cell comprising the vector of claim 16.

* * * * *

UNITED STATES PATENT AND TRADEMARK OFFICE
CERTIFICATE OF CORRECTION

| | |
|---|---|
| PATENT NO. | : 7,166,433 B2 |
| APPLICATION NO. | : 10/792307 |
| DATED | : January 23, 2007 |
| INVENTOR(S) | : Griffith et al. |

It is certified that error appears in the above-identified patent and that said Letters Patent is hereby corrected as shown below:

IN THE TITLE PAGE:

Item (54) "TRANSDUCTIN-1 AND TRANSDUCTIN-2 AND APPLICATIONS TO HEREDITARY DEAFNESS" should read -- TRANSDUCTIN-2 AND APPLICATIONS TO HEREDITARY DEAFNESS --.

Signed and Sealed this

Fourth Day of September, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 4333
<212> TYPE: DNA
<213> ORGANISM: Homo sapiens -continued

```
<400> SEQUENCE: 1
cagaaactat gagggcagaa cccagcaatc tgtgctttct tcacaagcc ctccaggagt      60 tgctgaaatt taggaatcat tgccccaaaa agtggccctc ataatgatgc cagatgggat     120
cttactctgt tgcccaggct ggagtgcagt ggtgcgatct cggctctctg caacctccgc     180
ctcccaggtt caagtgattc tcctgcctcg gcctcctgag tagctgggat tcaggccat      240 gaaagatcac tgttttagtc tgcgtggtgc agtggaacag atagacctcg gtttgaatct     300
cagctctact gtttactaga cgtgaaatgg ggaaatctaa aatgagatgc cagaagcctc     360
aaaaatggaa aaccccctgt gcttcacatc tgaaaatctc tgctggggc agcaactttg      420 agcctgtggg gaaggaactg tccacgtgga gtggtctggt gaatgcttaa ggagctgcag     480
aagggaagtc cctctccaaa ctagccagcc actgagacct tctgacagga caccccagg     540 atgtcaccca aaaagtaca atcaaagtg gaggaaaaag aagacgagac tgaggaaagc      600
tcaagtgaag aggaagagga ggtggaagat aagctacctc gaagagagag cttgagacca     660
aagaggaaac ggaccagaga tgttatcaat gaggatgacc cagaacctga accagaggat     720
gaagaaacaa ggaaggcaag agaaaaagag aggaggagga ggctaaagag aggagcagaa     780
aaagaagaaa ttgatgaaga ggaattggaa agattgaagg cagagttaga tgagaaaaga     840 caataattg ctactgtcaa atgcaaacca tggaagatgg agaagaaaat tgaagttctc     900
aaggaggcaa aaaaatttgt gagtgaaaat gaaggggctc ttgggaaagg aaaaggaaaa     960
cggtggtttg catttaagat gatgatggcc aagaaatggg caaaattcct ccgtgatttt    1020
gagaacttca agctgcgtg tgtcccatgg gaaaataaaa tcaaggctat tgaaagtcag    1080
tttggctcct cagtggcctc atacttcctc ttcttgagat ggatgtatgg agtcaatatg    1140
gttctcttta tcctgacatt tagcctcatc atgttgccag agtacctctg ggtttgcca    1200 tatggcagtt tacctaggaa aaccgttccc agagccgaag aggcatcggc agcaaacttt    1260
ggtgtgttgt acgacttcaa tggtttggca caatattccg ttctctttta tggctattat    1320
gacaataaac gaacaattgg atggatgaat tcaggttgc cgctctccta ttttctagtg     1380
gggattatgt gcattggata cagctttctg gttgtcctca agcaatgac caaaaacatt     1440 ggtgatgatg gaggtggaga tgacaacact tcaatttca gctggaaggt ctttaccagc    1500
tgggactacc tgatcggcaa tcctgaaaca gcagacaaca aatttaattc tatcacaatg    1560
aactttaagg aagctatcac agaagaaaaa gcagcccaag tagaagaaaa cgtccacttg    1620
atcagattcc tgaggtttct ggctaacttc ttcgtgtttc taacacttgg agggagtgga    1680
tacctcatct ttgggctgt gaagcgatcc aggaatttg cacagcaaga tcctgacacc    1740 cttggggtggt gggaaaaaaa tgaaatgaac atggttatgt ccctcctagg gatgttctgt    1800
ccaacattgt ttgacttatt tgctgaatta gaagactacc atcctctcat cgctttgaaa    1860
tggctactgg gacgcatttt tgctcttctt ttaggcaatt tatacgtatt tattcttgca    1920
ttaatggatg agattaacaa caagattgaa gaggagaagc tagtaaaggc caatattacc    1980
ctttgggaag ccaatatgat caaggcctac aatgcatcat tctctgaaaa tagcactgga    2040 ccacccttt tgttcacccc tgcagatgta cctcgaggac cttgctggga acaatggtg     2100 ggacaggagt ttgtgaggct gacagtctct gatgttctga ccacctacgt cacaatcctc    2160 attgggact ttctaagggc atgttttgtg aggttttgca attattgctg gtgctgggac    2220
ttggagtatg gatatccttc atacaccgaa ttcgacatca gtgggaacgt cctcgctctg    2280
atcttcaacc aaggcatgat ctggatgggc tccttctttg ctcccagcct cccaggcatc    2340
```

```
aatatccttc gactccatac atccatgtac ttccagtgct gggccgttat gtgctgcaat    2400
gttcctgagg ccagggtctt caaagcttcc agatcaaata acttctacct gggcatgcta    2460
ctgctcatcc tcttcctgtc cacaatgcct gtcttgtaca tgatcgtgtc cctcccacca    2520
tcttttgatt gtggtccatt cagtggcaaa atagaatgt ttgaagtcat tggagagacc     2580
ctggagcacg atttcccaag ctggatggcg aagatcttga gacagctttc aaaccctggg    2640
ctggtcattg ctgtcatttt ggtgatggtt ttggccatct attatctcaa tgctactgcc    2700
aagggccaga aggcagcgaa tctggatctc aaaaagaaga tgaaaatgca agctttggag    2760
aacaaaatgc gaaacaagaa atggcagct gcacgagcag ctgcagctgc tggtcgccag     2820
taataagtat cctgagagcc agaaaaggt acactttgcc ttgctgttta aaagtaatgc     2880
aatatgtgaa cgcccagaga caagcactg tggaactgct attttcctgt ctaccctig      2940 atggattttc aaggtcatgc tggccaatta aggcatcatc agtcctacct gagcaacaag    3000
aatctaaact ttattccaag tcagaaactg tttctgcaga gccactctct ccctgctcc     3060 atttcgtgac tttttttttt tttttaacaa attgagttta gaagtgagtg taatccagca    3120
atacagttta ctggtttagt tggtgggtta attaaaaaaa atttgctcat atgaactttc    3180
attttatatg tttctttgc ctgagtttcc ttaaactgag agcagaaata tttcacccctt    3240 tttcctctaa gttcagaaat atttgcaaaa agtactcatt gtaatcattc attaactcac    3300
tttttgaaac caatacctta ttttctcttt ttttctacct gtctccccaa ccacgcgccc    3360
cacaaatata ttcctaaaac ctttgtattt ggtgctggat tcagtatgaa aagaaatagg    3420
gtttttagaa gaaaaaaaaa tcctatatga attgggcct ggatagcact gaggttgaag     3480
atcttgaaga tctcttactt tgagaaggta catgagtctt acacaaccta gcttttatg     3540 agataaaatt aaaaaaaaaa ggaaagacat cataaatgac tgttgttctc tcacagtctg    3600
ctcatttgtc ttccaatgat catgttatca gtggtgaatc catacaggtc tgcatcaaac    3660
tcgatacaat tcttgcctcc ttggagggaa gaattcagct gaggggcaga agtaggttta    3720
tggcagaggg agagaatgag gcaagtttta gagcaggagt gtaggtttat taaaaagttt    3780
tacagcagga acaaaaggaa ataaaatata cttggaagag agccaagtgg gcaaattgag    3840
agttccaagt gccctgttca gctttgacct gggtttctat acactggcat ggttctggag    3900
tttgcatctc tccccgcttg attttttttgg cggatgggct gtccgtgtgg atggtggcct   3960
gccggcagtt ggaaggagct atgtgtacaa tgtgttactg aagttgtgtg cctgctcact    4020
tgtgacgttt tcccttacca tccagcgttc ctggaggaag gtcatatact agttaaactc    4080
tgccattttg cttagtgggc atgcttgagc ccacttgccc aactcctaag atctccggct    4140
caggtgtttt ctatctattg ggagactgtc tttccctagc actggttgcc actaattatt    4200
attttagaga gatagtttaa ccaccacctg accatcacca aatggtcacc tgacattcct    4260
gtgggatggg tggtgggggg cctctcttgc cctgcttatg ttttatgtt tgcctaacta     4320 cctactctaa caa                                                        4333
```

<210> SEQ ID NO 2
<211> LENGTH: 760
<212> TYPE: PRT
<213> ORGANISM: Homo sapiens

<400> SEQUENCE: 2

Met Ser Pro Lys Lys Val Gln Ile Lys Val Glu Glu Lys Glu Asp Glu
1               5                   10                  15

```
Thr Glu Glu Ser Ser Glu Glu Glu Glu Val Glu Asp Lys Leu
         20                  25              30

Pro Arg Arg Glu Ser Leu Arg Pro Lys Arg Lys Arg Thr Arg Asp Val
             35                  40                  45

Ile Asn Glu Asp Asp Pro Glu Pro Glu Pro Glu Asp Glu Glu Thr Arg
         50                  55                  60

Lys Ala Arg Glu Lys Glu Arg Arg Arg Leu Lys Arg Gly Ala Glu
65                  70                  75                  80

Lys Glu Glu Ile Asp Glu Glu Glu Leu Glu Arg Leu Lys Ala Glu Leu
                 85                  90                  95

Asp Glu Lys Arg Gln Ile Ile Ala Thr Val Lys Cys Lys Pro Trp Lys
             100                 105                 110

Met Glu Lys Lys Ile Glu Val Leu Lys Glu Ala Lys Lys Phe Val Ser
             115                 120                 125

Glu Asn Glu Gly Ala Leu Gly Lys Gly Lys Gly Lys Arg Trp Phe Ala
             130                 135                 140

Phe Lys Met Met Met Ala Lys Lys Trp Ala Lys Phe Leu Arg Asp Phe
145                 150                 155                 160

Glu Asn Phe Lys Ala Ala Cys Val Pro Trp Glu Asn Lys Ile Lys Ala
                 165                 170                 175

Ile Glu Ser Gln Phe Gly Ser Ser Val Ala Ser Tyr Phe Leu Phe Leu
             180                 185                 190

Arg Trp Met Tyr Gly Val Asn Met Val Leu Phe Ile Leu Thr Phe Ser
             195                 200                 205

Leu Ile Met Leu Pro Glu Tyr Leu Trp Gly Leu Pro Tyr Gly Ser Leu
210                 215                 220

Pro Arg Lys Thr Val Pro Arg Ala Glu Glu Ala Ser Ala Ala Asn Phe
225                 230                 235                 240

Gly Val Leu Tyr Asp Phe Asn Gly Leu Ala Gln Tyr Ser Val Leu Phe
                 245                 250                 255

Tyr Gly Tyr Tyr Asp Asn Lys Arg Thr Ile Gly Trp Met Asn Phe Arg
             260                 265                 270

Leu Pro Leu Ser Tyr Phe Leu Val Gly Ile Met Cys Ile Gly Tyr Ser
             275                 280                 285

Phe Leu Val Val Leu Lys Ala Met Thr Lys Asn Ile Gly Asp Asp Gly
             290                 295                 300

Gly Gly Asp Asp Asn Thr Phe Asn Phe Ser Trp Lys Val Phe Thr Ser
305                 310                 315                 320

Trp Asp Tyr Leu Ile Gly Asn Pro Glu Thr Ala Asp Asn Lys Phe Asn
                 325                 330                 335

Ser Ile Thr Met Asn Phe Lys Glu Ala Ile Thr Glu Lys Ala Ala
             340                 345                 350

Gln Val Glu Glu Asn Val His Leu Ile Arg Phe Leu Arg Phe Leu Ala
             355                 360                 365

Asn Phe Phe Val Phe Leu Thr Leu Gly Gly Ser Gly Tyr Leu Ile Phe
         370                 375                 380

Trp Ala Val Lys Arg Ser Gln Glu Phe Ala Gln Gln Asp Pro Asp Thr
385                 390                 395                 400

Leu Gly Trp Trp Glu Lys Asn Glu Met Asn Met Val Met Ser Leu Leu
                 405                 410                 415

Gly Met Phe Cys Pro Thr Leu Phe Asp Leu Phe Ala Glu Leu Glu Asp
             420                 425                 430
```

```
Tyr His Pro Leu Ile Ala Leu Lys Trp Leu Leu Gly Arg Ile Phe Ala
            435                 440                 445

Leu Leu Leu Gly Asn Leu Tyr Val Phe Ile Leu Ala Leu Met Asp Glu
450                 455                 460

Ile Asn Asn Lys Ile Glu Glu Lys Leu Val Lys Ala Asn Ile Thr
465                 470                 475                 480

Leu Trp Glu Ala Asn Met Ile Lys Ala Tyr Asn Ala Ser Phe Ser Glu
                485                 490                 495

Asn Ser Thr Gly Pro Pro Phe Val His Pro Ala Asp Val Pro Arg
                500                 505                 510

Gly Pro Cys Trp Glu Thr Met Val Gly Gln Glu Phe Val Arg Leu Thr
            515                 520                 525

Val Ser Asp Val Leu Thr Thr Tyr Val Thr Ile Leu Ile Gly Asp Phe
530                 535                 540

Leu Arg Ala Cys Phe Val Arg Phe Cys Asn Tyr Cys Trp Cys Trp Asp
545                 550                 555                 560

Leu Glu Tyr Gly Tyr Pro Ser Tyr Thr Glu Phe Asp Ile Ser Gly Asn
                565                 570                 575

Val Leu Ala Leu Ile Phe Asn Gln Gly Met Ile Trp Met Gly Ser Phe
                580                 585                 590

Phe Ala Pro Ser Leu Pro Gly Ile Asn Ile Leu Arg Leu His Thr Ser
            595                 600                 605

Met Tyr Phe Gln Cys Trp Ala Val Met Cys Cys Asn Val Pro Glu Ala
            610                 615                 620

Arg Val Phe Lys Ala Ser Arg Ser Asn Asn Phe Tyr Leu Gly Met Leu
625                 630                 635                 640

Leu Leu Ile Leu Phe Leu Ser Thr Met Pro Val Leu Tyr Met Ile Val
                645                 650                 655

Ser Leu Pro Pro Ser Phe Asp Cys Gly Pro Phe Ser Gly Lys Asn Arg
            660                 665                 670

Met Phe Glu Val Ile Gly Glu Thr Leu Glu His Asp Phe Pro Ser Trp
            675                 680                 685

Met Ala Lys Ile Leu Arg Gln Leu Ser Asn Pro Gly Leu Val Ile Ala
            690                 695                 700

Val Ile Leu Val Met Val Leu Ala Ile Tyr Tyr Leu Asn Ala Thr Ala
705                 710                 715                 720

Lys Gly Gln Lys Ala Ala Asn Leu Asp Leu Lys Lys Met Lys Met
                725                 730                 735

Gln Ala Leu Glu Asn Lys Met Arg Asn Lys Lys Met Ala Ala Ala Arg
            740                 745                 750

Ala Ala Ala Ala Ala Gly Arg Gln
            755                 760

<210> SEQ ID NO 3
<211> LENGTH: 3169
<212> TYPE: DNA
<213> ORGANISM: Homo sapiens

<400> SEQUENCE: 3
gcagtgctgc tgaccatgag ccaccaggta aagggcctga agaggaagc acgaggcgga      60 gtgaaagggc gggtgaagag cggctctcca cacacaggtg acaggctggg aaggagatcc    120
tcaagcaagc gggctctcaa agccgagggg accccaggca ggcgcggagc tcagcgaagc    180
cagaaggagc gcgccggggg cagcccaagc ccggggtctc cccggaggaa gcaaacaggg    240
```

-continued

| | |
|---|---|
| cgcaggagac acagagaaga gctgggggag caggagcggg gcgaggcaga gaggacctgc | 300 |
| gagggcagga gaaagcgcga cgagagggcc tccttccagg agcggacagc agccccaaag | 360 |
| agggaaaagg agattccgag gaaggaggag aagtcgaagc ggcagaagaa acccaggtca | 420 |
| tcctccttgg cctccagtgc ctctggtggg gagtccctgt ccgaggagga actggcccag | 480 |
| atcctggagc aggtggaaga aaaaaagaag ctcattgcca ccatgcggag caagccctgg | 540 |
| cccatggcga agaagctgac agagctcagg gaggcccagg aatttgtgga agagtatgaa | 600 |
| ggtgccttgg gaaaggggaa aggcaagcaa ctatatgcct acaagatgct gatggccaag | 660 |
| aaatgggtca aatttaagag agactttgat aatttcaaga ctcaatgtat ccctgggaa | 720 |
| atgaagatca aggacattga aagtcacttt ggttcttcag tggcatcgta tttcatcttt | 780 |
| ctccgatgga tgtatggagt taaccttgtc cttttggct taatatttgg tctagtcata | 840 |
| atcccagagg tactgatggg catgccctat gggagtattc ccagaaagac agtgcctcgg | 900 |
| gctgaggaag aaaaggccat ggattttct gtcctttggg attttgaggg ctatatcaag | 960 |
| tactctgcac tcttctatgg ctactacaac aaccagagga ccatcgggtg gctgaggtac | 1020 |
| cggctgccta tggcttactt tatggtgggg gtcagcgtgt tcggctacag cctgattatt | 1080 |
| gtcattcgat cgatggccag caatacccaa ggaagcacag gcgaagggga gagtgacaac | 1140 |
| ttcacattca gcttcaagat gttcaccagc tgggactacc tgatcgggaa ttcagagaca | 1200 |
| gctgataaca aatatgcatc catcaccacc agcttcaagg aatcaatagt ggatgaacaa | 1260 |
| gagagtaaca agaagaaaa tatccatctg acaagatttc ttcgtgtcct ggccaacttt | 1320 |
| ctcatcatct gctgtttgtg tggaagtggg tacctcattt actttgtggt taagcgatct | 1380 |
| cagcaattct ccaaaatgca gaatgtcagc tggtatgaaa ggaatgaggt agagatcgtg | 1440 |
| atgtccctgc ttggaatgtt ttgtcccct ctgtttgaaa ccatcgctgc cctggagaat | 1500 |
| taccacccac gcactggact gaagtggcag ctgggacgca tctttgcact cttcctgggg | 1560 |
| aacctctaca catttctctt ggccctgatg gatgacgtcc acctcaagct tgctaatgaa | 1620 |
| gagacaataa agaacatcac tcactggact ctgtttaact attacaactc ttctggttgg | 1680 |
| aacgagagtg tccccgacc acccctgcac cctgcagatg tgccccgggg ttcttgctgg | 1740 |
| gagacagctg tgggcattga attcatgagg ctgacggtgt ctgacatgct ggtaacgtac | 1800 |
| atcaccatcc tgctggggga cttcctacgg gcttgttttg tgcggttcat gaactactgc | 1860 |
| tggtgctggg acttggaggc tggatttcct tcatatgctg agtttgatat tagtggaaat | 1920 |
| gtgctgggtt tgatcttcaa ccaaggaatg atctggatgg ctccttcta tgctccaggc | 1980 |
| ctggtgggca ttaatgtgct gcgcctgctg acctccatgt acttccagtg ctgggcggtg | 2040 |
| atgagcagca acgtaccca tgaacgcgtg ttcaaagcct cccgatccaa caacttctac | 2100 |
| atgggcctcc tgctgctggt gctcttcctc agcctcctgc cggtggccta caccatcatg | 2160 |
| tccctcccac cctcctttga ctgcgggccg ttcagtggga aaaacagaat gtacgatgtc | 2220 |
| ctccaagaga ccattgaaaa cgatttccca accttcctgg gcaagatctt gctttcctc | 2280 |
| gccaatccag gctgatcat cccagccatc ctgctgatgt tcttggccat ttactacctg | 2340 |
| aactcagttt ccaaaagcct ttcccgagct aatgcccagc tgaggaagaa aatccaagtg | 2400 |
| ctccgtgaag ttgagaagag tcacaaatct gtaaaaggca aagccacagc cagagattca | 2460 |
| gaggacacac ctaaaagcag ctccaaaaat gccacccagc tccaactcac caaggaagag | 2520 |
| accactcctc cctctgccag ccaaagccag gccatggaca gaaggcgca gggcctgggg | 2580 |
| acctccaatt ctgccagcag gaccacactg cctgcctctg gacaccttcc tatatctcgg | 2640 |

```
cccnctggaa tcggaccaga ttctggccac gccccatctc agactcatcc gtggaggtca    2700
gcctctggaa agagtgctca gagacctccc cactgacggc taggactcca gggagcctcg    2760
accctagggc tgatcctcaa gtaccccagt ttcacacata ccaaaccaag gttctctccc    2820
ctctttcctc tcacatacat gctctgtctc ctctcttgga atgcatgaac tttgattcct    2880
tcaggccctt gtcagctacc gaaggaggaa gacagtggct tcacctgtcc tttagggaag    2940
ctggagccat ctctgcacta actgccctcc caaatatctt ggttcagaca gctctgaacc    3000
ccacgctcac agtggtcgac cttgcctccc gattttcgga gttggggaag ggccatgacc    3060
accctcgtag actttttcca tgggatacag tttaggacac gggtttctgc cagcttccct    3120
aaccaggagg gggatggaga agggcctaca tttctcaatc cagaggaag              3169
```

<210> SEQ ID NO 4
<211> LENGTH: 906
<212> TYPE: PRT
<213> ORGANISM: Homo sapiens

<400> SEQUENCE: 4

```
Met Ser His Gln Val Lys Gly Leu Lys Glu Glu Ala Arg Gly Gly Val
1               5                   10                  15

Lys Gly Arg Val Lys Ser Gly Ser Pro His Thr Gly Asp Arg Leu Gly
                20                  25                  30

Arg Arg Ser Ser Ser Lys Arg Ala Leu Lys Ala Glu Gly Thr Pro Gly
            35                  40                  45

Arg Arg Gly Ala Gln Arg Ser Gln Lys Glu Arg Ala Gly Gly Ser Pro
        50                  55                  60

Ser Pro Gly Ser Pro Arg Arg Lys Gln Thr Gly Arg Arg Arg His Arg
65                  70                  75                  80

Glu Glu Leu Gly Glu Gln Glu Arg Gly Glu Ala Glu Arg Thr Cys Glu
                85                  90                  95

Gly Arg Arg Lys Arg Asp Glu Arg Ala Ser Phe Gln Glu Arg Thr Ala
            100                 105                 110

Ala Pro Lys Arg Glu Lys Glu Ile Pro Arg Lys Glu Lys Ser Lys
        115                 120                 125

Arg Gln Lys Lys Pro Arg Ser Ser Ser Leu Ala Ser Ser Ala Ser Gly
130                 135                 140

Gly Glu Ser Leu Ser Glu Glu Leu Ala Gln Ile Leu Glu Gln Val
145                 150                 155                 160

Glu Glu Lys Lys Lys Leu Ile Ala Thr Met Arg Ser Lys Pro Trp Pro
                165                 170                 175

Met Ala Lys Lys Leu Thr Glu Leu Arg Glu Ala Gln Glu Phe Val Glu
            180                 185                 190

Lys Tyr Glu Gly Ala Leu Gly Lys Gly Lys Gly Lys Gln Leu Tyr Ala
        195                 200                 205

Tyr Lys Met Leu Met Ala Lys Lys Trp Val Lys Phe Lys Arg Asp Phe
    210                 215                 220

Asp Asn Phe Lys Thr Gln Cys Ile Pro Trp Glu Met Lys Ile Lys Asp
225                 230                 235                 240

Ile Glu Ser His Phe Gly Ser Ser Val Ala Ser Tyr Phe Ile Phe Leu
                245                 250                 255

Arg Trp Met Tyr Gly Val Asn Leu Val Leu Phe Gly Leu Ile Phe Gly
            260                 265                 270

Leu Val Ile Ile Pro Glu Val Leu Met Gly Met Pro Tyr Gly Ser Ile
```

```
            275                 280                 285
Pro Arg Lys Thr Val Pro Arg Ala Glu Glu Lys Ala Met Asp Phe
    290                 295                 300

Ser Val Leu Trp Asp Phe Glu Gly Tyr Ile Lys Tyr Ser Ala Leu Phe
305                 310                 315                 320

Tyr Gly Tyr Tyr Asn Asn Gln Arg Thr Ile Gly Trp Leu Arg Tyr Arg
                325                 330                 335

Leu Pro Met Ala Tyr Phe Met Val Gly Val Ser Val Phe Gly Tyr Ser
                340                 345                 350

Leu Ile Ile Val Ile Arg Ser Met Ala Ser Asn Thr Gln Gly Ser Thr
                355                 360                 365

Gly Glu Gly Glu Ser Asp Asn Phe Thr Phe Ser Phe Lys Met Phe Thr
    370                 375                 380

Ser Trp Asp Tyr Leu Ile Gly Asn Ser Glu Thr Ala Asp Asn Lys Tyr
385                 390                 395                 400

Ala Ser Ile Thr Thr Ser Phe Lys Glu Ser Ile Val Asp Glu Gln Glu
                405                 410                 415

Ser Asn Lys Glu Glu Asn Ile His Leu Thr Arg Phe Leu Arg Val Leu
                420                 425                 430

Ala Asn Phe Leu Ile Ile Cys Cys Leu Cys Gly Ser Gly Tyr Leu Ile
                435                 440                 445

Tyr Phe Val Val Lys Arg Ser Gln Gln Phe Ser Lys Met Gln Asn Val
            450                 455                 460

Ser Trp Tyr Glu Arg Asn Glu Val Glu Ile Val Met Ser Leu Leu Gly
465                 470                 475                 480

Met Phe Cys Pro Pro Leu Phe Glu Thr Ile Ala Ala Leu Glu Asn Tyr
                485                 490                 495

His Pro Arg Thr Gly Leu Lys Trp Gln Leu Gly Arg Ile Phe Ala Leu
                500                 505                 510

Phe Leu Gly Asn Leu Tyr Thr Phe Leu Leu Ala Leu Met Asp Asp Val
            515                 520                 525

His Leu Lys Leu Ala Asn Glu Glu Thr Ile Lys Asn Ile Thr His Trp
    530                 535                 540

Thr Leu Phe Asn Tyr Tyr Asn Ser Ser Gly Trp Asn Glu Ser Val Pro
545                 550                 555                 560

Arg Pro Pro Leu His Pro Ala Asp Val Pro Arg Gly Ser Cys Trp Glu
                565                 570                 575

Thr Ala Val Gly Ile Glu Phe Met Arg Leu Thr Val Ser Asp Met Leu
                580                 585                 590

Val Thr Tyr Ile Thr Ile Leu Leu Gly Asp Phe Leu Arg Ala Cys Phe
            595                 600                 605

Val Arg Phe Met Asn Tyr Cys Trp Cys Trp Asp Leu Glu Ala Gly Phe
    610                 615                 620

Pro Ser Tyr Ala Glu Phe Asp Ile Ser Gly Asn Val Leu Gly Leu Ile
625                 630                 635                 640

Phe Asn Gln Gly Met Ile Trp Met Gly Ser Phe Tyr Ala Pro Gly Leu
                645                 650                 655

Val Gly Ile Asn Val Leu Arg Leu Leu Thr Ser Met Tyr Phe Gln Cys
                660                 665                 670

Trp Ala Val Met Ser Ser Asn Val Pro His Glu Arg Val Phe Lys Ala
            675                 680                 685

Ser Arg Ser Asn Asn Phe Tyr Met Gly Leu Leu Leu Leu Val Leu Phe
    690                 695                 700
```

-continued

```
Leu Ser Leu Leu Pro Val Ala Tyr Thr Ile Met Ser Leu Pro Pro Ser
705                 710                 715                 720
Phe Asp Cys Gly Pro Phe Ser Gly Lys Asn Arg Met Tyr Asp Val Leu
            725                 730                 735
Gln Glu Thr Ile Glu Asn Asp Phe Pro Thr Phe Leu Gly Lys Ile Phe
        740                 745                 750
Ala Phe Leu Ala Asn Pro Gly Leu Ile Ile Pro Ala Ile Leu Leu Met
                755                 760                 765
Phe Leu Ala Ile Tyr Tyr Leu Asn Ser Val Ser Lys Ser Leu Ser Arg
    770                 775                 780
Ala Asn Ala Gln Leu Arg Lys Lys Ile Gln Val Leu Arg Glu Val Glu
785                 790                 795                 800
Lys Ser His Lys Ser Val Lys Gly Lys Ala Thr Ala Arg Asp Ser Glu
            805                 810                 815
Asp Thr Pro Lys Ser Ser Lys Asn Ala Thr Gln Leu Gln Leu Thr
        820                 825                 830
Lys Glu Glu Thr Thr Pro Pro Ser Ala Ser Gln Ser Gln Ala Met Asp
835                 840                 845
Lys Lys Ala Gln Gly Pro Gly Thr Ser Asn Ser Ala Ser Arg Thr Thr
850                 855                 860
Leu Pro Ala Ser Gly His Leu Pro Ile Ser Arg Pro Pro Gly Ile Gly
865                 870                 875                 880
Pro Asp Ser Gly His Ala Pro Ser Gln Thr His Pro Trp Arg Ser Ala
                885                 890                 895
Ser Gly Lys Ser Ala Gln Arg Pro Pro His
            900                 905
```

<210> SEQ ID NO 5
<211> LENGTH: 2895
<212> TYPE: DNA
<213> ORGANISM: Mus musculus

<400> SEQUENCE: 5

```
ttgcaattcc tgattagaga cattctggca ggataccttc aggatgccac ccaaaaaagg      60
tgtgtctggc catttctgat gcaargktgc ctgtcttcct cttarctcct gtcctggaca     120
ttcattatca aggcacaaga ttacattcct cctcaactct tttatgttgc aaatccaagt     180
ggaggagaaa gaagaggata cagaggaaag ctcaagtgaa gaagaagaag ataagctacc     240
cagaagagag agcttgagac caaagaggaa acggaccaga gatgtcatca atgaggatga     300
cccagaaccg gagccggagg atgaagaaac aagaaaggca agagaaaaag aaaggcggag     360
gaggctgcgg agaggagcgg aagaagaaga agaaattgat gaagaggaat tagaacggtt     420
aaaagcactg ctcgatgaga atagacaaat gatcgctact gtcaaatgta aaccttggaa     480
aatggagaag aaaattgaag ttctcaagga agcaaagaaa tttgtgagtg agaatgaagg     540
cgctcttggg aaaggaaagg gaaagaagtg gtttgcattt aagatgatga tggccaagaa     600
atgggcaaaa ttcctccgag attttgagaa cttcaaagcg gcttgcgtcc catgggaaaa     660
caaaatcaag gcaattgaaa gtcagtttgg ttcctcagtg gcctcgtact tcctgttcct     720
caggtggatg tacggcgtca acatggttct ctttgtgttg accttcagcc tcatcatgtt     780
accggagtac ctctggggtt taccgtacgg cagcttacct aggaaaacag tcccaagagc     840
tgaagaagca tctgcagcca actttggtgt gttgtatgac ttcaatgcc tggcgcagta     900
ctctgtcctc ttttatggct attacgacaa taaacgcacg atcggatggc tgaatttccg     960
```

-continued

```
gctacctctt tcctacttcc tggtggggat tatgtgcatt ggatacagct tcctggttgt    1020
cctcaaagcg atgaccaaaa atattggtga cgatggtggt ggcgatgaca cactttcaa    1080
cttcagctgg aaggtgttct gtagctggga ctatctgatt ggtaaccctg aaacagccga    1140
caacaagttt aactctatca cgatgaactt taaggaagcc atcatagaag agagagccgc    1200
acaggtggag gagaacatcc acctcatcag atttctgagg tttctcgcta acttcttcgt    1260
gttcctcaca cttggtgcaa gtggatacct catcttttgg gctgtgaagc gatcccagga    1320
gttcgcccag caagatcctg caccctttgg gtggtgggaa aaaaatgaaa tgaacatggt    1380
aatgtccctc ctggggatgt tctgtcccac cctgtttgac ttatttgctg aactggaaga    1440
ttaccatcct ctcattgctc tgaagtggcc cctggggcgc atttttgctc ttcttctagg    1500
caacttgtat gtattcattc tcgccttgat ggatgagatt aacaacaaga ttgaagagga    1560
gaagcttgtg aaggctaata ttaccctgtg gaagccaac atgattaagg cttacaatga    1620
atctctctct gggctctctg gaacaccac aggagcaccc tttttcgttc atcctgcaga    1680
tgtccctcgc ggtccctgct gggaaacaat ggtggggcag gaattcgtgc gtctcaccgt    1740
ttctgacgtc ctgaccactt acgtcacgat cctcattggc gacttcctca gagcatgttt    1800
cgtgaggttc tgcaattact gctggtgctg ggacttagaa tatggatatc cttcatacac    1860
agaattcgac atcagtggca acgtcctcgc tctgatcttc aaccaaggca tgatctggat    1920
gggctccttc ttcgctccta gcctcccggg catcaacatc ctccgtctcc acacatccat    1980
gtatttccag tgctgggctg tgatgtgctg caatgttccc gaggcagggg tgttcaaagc    2040
ttccagatcc aacaacttct acctcggcat gctgctactc atcctcttcc tgtccaccat    2100
gccagtcctg tacatgatcg tctccctccc gccatcttt gattgtgggc cttcagtgg    2160
taaaaacagg atgtttgaag tcatcggtga cccctggaa catgacttcc caagctggat    2220
ggcgaagatc ctgaggcagc tttctaaccc cggccttgtc attgctgtca ttctggtgat    2280
ggtcctgacc atctattatc tcaatgctac tgccaagggc cagaaagcag cgaatctgga    2340
cctcaaaaag aagatgaaac agcaagcttt ggagaacaaa atgcgaaaca gaaaatggc    2400
agcggctcga gcagctgcag ctgctggtgg ccagtaattt tatcaaatgt cctggaggtg    2460
cccagaagta ctcttcactt ctgtctttgt atggacagag tgagggccag tgaactgctg    2520
ctctatactc taccaccaat gcaccatcat ggcygcagtc atgaccatct gkcaaggaat    2580
catcagccct ctttgarcaa raaraatctc accattattt atgggaatt tttcaaagaa    2640
ttcttgaact cctcttcttc tctytctctc ctggacaaag kttctcaaac aaatgggagt    2700
ttaaatgtgg gtgtgatgta gtgatacaaa ttactgggta aaaatgatag gatactttaa    2760
aaaagtcaac atttcctcat atggactttt tcttacacac tggtctagtt tcttaaatga    2820
gaggagagct attacaacat cctttgctat ctaaaттттgg aactatctgc atgaagcatt    2880
ccttgggatc attca                                                    2895
```

<210> SEQ ID NO 6
<211> LENGTH: 757
<212> TYPE: PRT
<213> ORGANISM: Mus musculus

<400> SEQUENCE: 6

Met Leu Gln Ile Gln Val Glu Glu Lys Glu Glu Asp Thr Glu Glu Ser
1               5                   10                  15

Ser Ser Glu Glu Glu Glu Asp Lys Leu Pro Arg Arg Glu Ser Leu Arg

-continued

```
                  20                  25                  30
Pro Lys Arg Lys Arg Thr Arg Asp Val Ile Asn Glu Asp Pro Glu
         35                  40                  45
Pro Glu Pro Glu Asp Glu Thr Arg Lys Ala Arg Glu Lys Glu Arg
 50                  55                  60
Arg Arg Arg Leu Arg Gly Ala Glu Glu Glu Glu Ile Asp Glu
 65                  70                  75                  80
Glu Glu Leu Glu Arg Leu Lys Ala Leu Leu Asp Glu Asn Arg Gln Met
                 85                  90                  95
Ile Ala Thr Val Lys Cys Lys Pro Trp Lys Met Glu Lys Lys Ile Glu
             100                 105                 110
Val Leu Lys Glu Ala Lys Lys Phe Val Ser Glu Asn Glu Gly Ala Leu
             115                 120                 125
Gly Lys Gly Lys Gly Lys Lys Trp Phe Ala Phe Lys Met Met Met Ala
             130                 135                 140
Lys Lys Trp Ala Lys Phe Leu Arg Asp Phe Glu Asn Phe Lys Ala Ala
145                 150                 155                 160
Cys Val Pro Trp Glu Asn Lys Ile Lys Ala Ile Glu Ser Gln Phe Gly
                 165                 170                 175
Ser Ser Val Ala Ser Tyr Phe Leu Phe Leu Arg Trp Met Tyr Gly Val
             180                 185                 190
Asn Met Val Leu Phe Val Leu Thr Phe Ser Leu Ile Met Leu Pro Glu
         195                 200                 205
Tyr Leu Trp Gly Leu Pro Tyr Gly Ser Leu Pro Arg Lys Thr Val Pro
     210                 215                 220
Arg Ala Glu Glu Ala Ser Ala Ala Asn Phe Gly Val Leu Tyr Asp Phe
225                 230                 235                 240
Asn Gly Leu Ala Gln Tyr Ser Val Leu Phe Tyr Gly Tyr Tyr Asp Asn
                 245                 250                 255
Lys Arg Thr Ile Gly Trp Leu Asn Phe Arg Leu Pro Leu Ser Tyr Phe
             260                 265                 270
Leu Val Gly Ile Met Cys Ile Gly Tyr Ser Phe Leu Val Val Leu Lys
         275                 280                 285
Ala Met Thr Lys Asn Ile Gly Asp Asp Gly Gly Asp Asp Asn Thr
     290                 295                 300
Phe Asn Phe Ser Trp Lys Val Phe Cys Ser Trp Asp Tyr Leu Ile Gly
305                 310                 315                 320
Asn Pro Glu Thr Ala Asp Asn Lys Phe Asn Ser Ile Thr Met Asn Phe
                 325                 330                 335
Lys Glu Ala Ile Ile Glu Glu Arg Ala Ala Gln Val Glu Glu Asn Ile
             340                 345                 350
His Leu Ile Arg Phe Leu Arg Phe Leu Ala Asn Phe Val Phe Leu
         355                 360                 365
Thr Leu Gly Ala Ser Gly Tyr Leu Ile Phe Trp Ala Val Lys Arg Ser
     370                 375                 380
Gln Glu Phe Ala Gln Gln Asp Pro Asp Thr Leu Gly Trp Trp Glu Lys
385                 390                 395                 400
Asn Glu Met Asn Met Val Met Ser Leu Leu Gly Met Phe Cys Pro Thr
                 405                 410                 415
Leu Phe Asp Leu Phe Ala Glu Leu Glu Asp Tyr His Pro Leu Ile Ala
             420                 425                 430
Leu Lys Trp Leu Leu Gly Arg Ile Phe Ala Leu Leu Leu Gly Asn Leu
         435                 440                 445
```

```
Tyr Val Phe Ile Leu Ala Leu Met Asp Glu Ile Asn Asn Lys Ile Glu
    450                 455                 460

Glu Glu Lys Leu Val Lys Ala Asn Ile Thr Leu Trp Glu Ala Asn Met
465                 470                 475                 480

Ile Lys Ala Tyr Asn Glu Ser Leu Ser Gly Leu Ser Gly Asn Thr Thr
                485                 490                 495

Gly Ala Pro Phe Phe Val His Pro Ala Asp Val Pro Arg Gly Pro Cys
                500                 505                 510

Trp Glu Thr Met Val Gly Gln Glu Phe Val Arg Leu Thr Val Ser Asp
            515                 520                 525

Val Leu Thr Thr Tyr Val Thr Ile Leu Ile Gly Asp Phe Leu Arg Ala
    530                 535                 540

Cys Phe Val Arg Phe Cys Asn Tyr Cys Trp Cys Trp Asp Leu Glu Tyr
545                 550                 555                 560

Gly Tyr Pro Ser Tyr Thr Glu Phe Asp Ile Ser Gly Asn Val Leu Ala
                565                 570                 575

Leu Ile Phe Asn Gln Gly Met Ile Trp Met Gly Ser Phe Phe Ala Pro
                580                 585                 590

Ser Leu Pro Gly Ile Asn Ile Leu Arg Leu His Thr Ser Met Tyr Phe
            595                 600                 605

Gln Cys Trp Ala Val Met Cys Cys Asn Val Pro Glu Ala Arg Val Phe
    610                 615                 620

Lys Ala Ser Arg Ser Asn Asn Phe Tyr Leu Gly Met Leu Leu Leu Ile
625                 630                 635                 640

Leu Phe Leu Ser Thr Met Pro Val Leu Tyr Met Ile Val Ser Leu Pro
                645                 650                 655

Pro Ser Phe Asp Cys Gly Pro Phe Ser Gly Lys Asn Arg Met Phe Glu
                660                 665                 670

Val Ile Gly Glu Thr Leu Glu His Asp Phe Pro Ser Trp Met Ala Lys
            675                 680                 685

Ile Leu Arg Gln Leu Ser Asn Pro Gly Leu Val Ile Ala Val Ile Leu
    690                 695                 700

Val Met Val Leu Thr Ile Tyr Tyr Leu Asn Ala Thr Ala Lys Gly Gln
705                 710                 715                 720

Lys Ala Ala Asn Leu Asp Leu Lys Lys Met Lys Gln Gln Ala Leu
                725                 730                 735

Glu Asn Lys Met Arg Asn Lys Lys Met Ala Ala Arg Ala Ala Ala
                740                 745                 750

Ala Ala Gly Gly Gln
        755

<210> SEQ ID NO 7
<211> LENGTH: 3216
<212> TYPE: DNA
<213> ORGANISM: Mus musculus

<400> SEQUENCE: 7
tgcaagagtg gccaagtttg ccgggcgtgg tggcacacgc ctttaatccg agcactcggg      60
aggcagagga aggcgaattt ctgagttcaa ggccagcctg gtctacaaag tgagttccag     120
gacagccagg gctacacaga gaaaccctgt ctccaaaaac caaaaaaaaa aaaaaaaata     180
gtggccaagt tgttccaga ggcccctagt tgccgtcagg ttccaggaag aggccagtga      240
ccatgacagc aggaagtcac cccaggctgg gcagtatatg aagacgtgag ccagtgtgag     300
```

```
ggccttgaaa ctctggtaac catgagcccc cagttaaaga gcttggacga ggaaggtgac      360
aagtcagcaa ggagacccac aaggaaacaa acctccagag ctgcatgtcc ccaagacggg      420
caccgagccc aatctagccg gaaggatcct gctaagggta gcccaagacc agggtcttcc      480
cggaagaaac agatggaaca tggaagctat cacaaggggt gcagggaca gaaaccacga       540 aaggtggaga ggtctctaca ggggaggaag aaggaccgga gaacttccct taaggagcag      600
agagcatctc caaagaagga gagggaggct ctgaggaagg aggcaggcaa gcagctgaga      660
aaacccaggt ccacttcctt gggctccagt gtctctactg gagactccct gtctgaggag      720
gagctggctc agatcctgga acaggtagaa gaaaaaaaga agctcatcac taccgtgagg      780
aacaaaccct ggcccatggc aaagaagctg agggaactca gggaagccca agcctttgtg      840
gagaagtatg aaggagcctt ggggaaaggc aagggcaaac acctctacgc ctacaggatg      900
atgatggcta agaaatgggt caagtttaag agggactttg ataatttcaa gactcaatgt      960
attccctggg aaatgaagat caaggacatt gaaagtcact tcggttcttc tgtggcatct     1020
tacttcatct ttctccgatg gatgtatgga gttaaccttg ccttttttgg cttaatattt     1080
ggtctagtca tcatcccaga ggtgctgatg ggcatgccct atggaagtat acccagaaag     1140
acggtgcctc gagctgagga agagcgagcc atggacttct ctgtcctttg ggattttgag     1200
ggctacatca aatattctgc tctcttctat ggctactaca caaccagcg gaccattgga      1260 tggctgaggt acaggctgcc catggcttac tttatggtgg gggtcagcgt gtttggctac     1320
agcttgatga tcgtcattag gtcgatggcc agcaataccc agggtagcac cagtgagggg     1380
gacagtgaca gcttcacatt cagcttcaag atgttccacca gctgggacta cctcatcggg     1440
aattcagaga cagcagacaa caaatatgtc tccatcacta ccagcttcaa ggagtctata     1500
gtggacgaac aagagagtaa caaagaaggg aatatccacc tgacaagatt cctccgcgtc     1560
ctggccaact ttctcattct ctgctgtctg tgtggaagcg ggtacctcat ttactttgtg     1620
gtgaaacggt cccaggagtt ctccaaaatg caaaatgtca gctggtatga aaggaatgag     1680
gtggagatcg tgatgtcttt gctagggatg ttttgtcccc ctctgtttga accatcgct      1740 gccttggaga attatcaccc acgaactggg ctgaagtggc agctgggccg catctttgcc     1800
ctcttcctgg gaaacctcta cacgtttctc ctggccctca tggacgatgt ccacttaag      1860 cttttctaatg aggaaaaaat caagaacatc actcactgga ccctgtttaa ctattacaat     1920
tcctcaggtg ggaatgagag tgtgccccgg ccaccaccac accctgcaga tgtgcccaga     1980
ggttcttgct gggagacagc tgtgggcatt gagtttatga ggctcaccgt gtctgacatg     2040
ctggtaacat acctcaccat cttggtcgga gatttcctcc gagcttgttt tgtccggttc     2100
atgaatcact gctggtgttg ggaccctcag gctggttttc cctcatatgc cgagtttgat     2160
attagtggaa atgtgttggg tttgatcttc aaccaaggaa tgatctggat gggctccttc     2220
tatgctccag gactggtggg catcaatgtc ctgcgcctgt tgacctccat gtacttccag     2280
tgctgggcag tgatgagcag caacgttccc cacgaacgtg tgtttaaagc ctccagatcc     2340
aacaacttct acatgggcct gctgctgttg gtgctcttcc tcagcctcct gcctgtggcc     2400
tacaccgtca tgtctctccc accctcgttt gactgtggcc ccttcagtgg gaaaaacaga     2460
atgtacgatg tcctccatga gaccatcgag aacgatttcc ctaagttcct gggcaagatc     2520
tttgcgttcc ttgccaaccc aggcctgatc attccagcca tcctgctaat gtttctggcc     2580
atttactatc tgaactcagt ttcaaaaagt ctttctagag ctaatgccca gctgcgaaag     2640
aagatccaag cgctccgtga agttgagaag aaccataaat ccatcaaggg aaaagccata     2700
```

-continued

```
gtcacatatt cagaggacac aatcaagaac agctccaaaa atgccaccca gatacatctt    2760
actaaagaag agcccacatc tcactcttcc agccaaatcc agaccctgga caagaaagcg    2820
cagggccccc acacctccag tactgagggt ggggcctcgc catctacctc ctggcaccat    2880
gttgggtctc aaccaccgag aggcagacga gattctggcc aaccccagtc tcagacttac    2940
acaggcaggt caccttctgg aaagagaacc cagaggcctc acaactgatt tctggcatt     3000 catgggtgtc ccagtccttg gcttgaatct ctactgtttt atatatctct tcccttctca    3060
tctcacatat acaaatgttt ccctatggct tatgtaacat atgaacttta atccttgctt    3120
ccagcccttg attactacct aaagggaaga gcaatggacc tcacacacta gcggtttcct    3180
ttggctccag acttgaggag gcagggatga ggccat                              3216
```

<210> SEQ ID NO 8
<211> LENGTH: 888
<212> TYPE: PRT
<213> ORGANISM: Mus musculus

<400> SEQUENCE: 8

```
Met Ser Pro Gln Leu Lys Ser Leu Asp Glu Glu Gly Asp Lys Ser Ala
1               5                   10                  15

Arg Arg Pro Thr Arg Lys Gln Thr Ser Arg Ala Ala Cys Pro Gln Asp
            20                  25                  30

Gly His Arg Ala Gln Ser Ser Arg Lys Asp Pro Ala Lys Gly Ser Pro
        35                  40                  45

Arg Pro Gly Ser Ser Arg Lys Lys Gln Met Glu His Gly Ser Tyr His
    50                  55                  60

Lys Gly Leu Gln Gly Gln Lys Pro Arg Lys Val Glu Arg Ser Leu Gln
65                  70                  75                  80

Gly Arg Lys Lys Asp Arg Arg Thr Ser Leu Lys Glu Gln Arg Ala Ser
                85                  90                  95

Pro Lys Lys Glu Arg Glu Ala Leu Arg Lys Glu Ala Gly Lys Gln Leu
            100                 105                 110

Arg Lys Pro Arg Ser Thr Ser Leu Gly Ser Ser Val Ser Thr Gly Asp
        115                 120                 125

Ser Leu Ser Glu Glu Glu Leu Ala Gln Ile Leu Glu Gln Val Glu Glu
    130                 135                 140

Lys Lys Lys Leu Ile Thr Thr Val Arg Asn Lys Pro Trp Pro Met Ala
145                 150                 155                 160

Lys Lys Leu Arg Glu Leu Arg Glu Ala Gln Ala Phe Val Glu Lys Tyr
                165                 170                 175

Glu Gly Ala Leu Gly Lys Gly Lys Gly Lys His Leu Tyr Ala Tyr Arg
            180                 185                 190

Met Met Met Ala Lys Lys Trp Val Lys Phe Lys Arg Asp Phe Asp Asn
        195                 200                 205

Phe Lys Thr Gln Cys Ile Pro Trp Glu Met Lys Ile Lys Asp Ile Glu
    210                 215                 220

Ser His Phe Gly Ser Ser Val Ala Ser Tyr Phe Ile Phe Leu Arg Trp
225                 230                 235                 240

Met Tyr Gly Val Asn Leu Val Leu Phe Gly Leu Ile Phe Gly Leu Val
                245                 250                 255

Ile Ile Pro Glu Val Leu Met Gly Met Pro Tyr Gly Ser Ile Pro Arg
            260                 265                 270

Lys Thr Val Pro Arg Ala Glu Glu Glu Arg Ala Met Asp Phe Ser Val
```

-continued

```
             275                 280                 285
Leu Trp Asp Phe Glu Gly Tyr Ile Lys Tyr Ser Ala Leu Phe Tyr Gly
    290                 295                 300
Tyr Tyr Asn Asn Gln Arg Thr Ile Gly Trp Leu Arg Tyr Arg Leu Pro
305                 310                 315                 320
Met Ala Tyr Phe Met Val Gly Val Ser Val Phe Gly Tyr Ser Leu Met
                325                 330                 335
Ile Val Ile Arg Ser Met Ala Ser Asn Thr Gln Gly Ser Thr Ser Glu
                340                 345                 350
Gly Asp Ser Asp Ser Phe Thr Phe Ser Phe Lys Met Phe Thr Ser Trp
                355                 360                 365
Asp Tyr Leu Ile Gly Asn Ser Glu Thr Ala Asp Asn Lys Tyr Val Ser
    370                 375                 380
Ile Thr Thr Ser Phe Lys Glu Ser Ile Val Asp Gln Glu Ser Asn
385                 390                 395                 400
Lys Glu Gly Asn Ile His Leu Thr Arg Phe Leu Arg Val Leu Ala Asn
                405                 410                 415
Phe Leu Ile Leu Cys Leu Cys Gly Ser Gly Tyr Leu Ile Tyr Phe
                420                 425                 430
Val Val Lys Arg Ser Gln Glu Phe Ser Lys Met Gln Asn Val Ser Trp
    435                 440                 445
Tyr Glu Arg Asn Glu Val Glu Ile Val Met Ser Leu Leu Gly Met Phe
    450                 455                 460
Cys Pro Pro Leu Phe Glu Thr Ile Ala Ala Leu Glu Asn Tyr His Pro
465                 470                 475                 480
Arg Thr Gly Leu Lys Trp Gln Leu Gly Arg Ile Phe Ala Leu Phe Leu
                485                 490                 495
Gly Asn Leu Tyr Thr Phe Leu Leu Ala Leu Met Asp Asp Val His Leu
                500                 505                 510
Lys Leu Ser Asn Glu Glu Lys Ile Lys Asn Ile Thr His Trp Thr Leu
                515                 520                 525
Phe Asn Tyr Tyr Asn Ser Ser Gly Gly Asn Glu Ser Val Pro Arg Pro
    530                 535                 540
Pro Pro His Pro Ala Asp Val Pro Arg Gly Ser Cys Trp Glu Thr Ala
545                 550                 555                 560
Val Gly Ile Glu Phe Met Arg Leu Thr Val Ser Asp Met Leu Val Thr
                565                 570                 575
Tyr Leu Thr Ile Leu Val Gly Asp Phe Leu Arg Ala Cys Phe Val Arg
                580                 585                 590
Phe Met Asn His Cys Trp Cys Trp Asp Leu Glu Ala Gly Phe Pro Ser
                595                 600                 605
Tyr Ala Glu Phe Asp Ile Ser Gly Asn Val Leu Gly Leu Ile Phe Asn
    610                 615                 620
Gln Gly Met Ile Trp Met Gly Ser Phe Tyr Ala Pro Gly Leu Val Gly
625                 630                 635                 640
Ile Asn Val Leu Arg Leu Leu Thr Ser Met Tyr Phe Gln Cys Trp Ala
                645                 650                 655
Val Met Ser Ser Asn Val Pro His Glu Arg Val Phe Lys Ala Ser Arg
                660                 665                 670
Ser Asn Asn Phe Tyr Met Gly Leu Leu Leu Val Leu Phe Leu Ser
    675                 680                 685
Leu Leu Pro Val Ala Tyr Thr Val Met Ser Leu Pro Pro Ser Phe Asp
    690                 695                 700
```

```
Cys Gly Pro Phe Ser Gly Lys Asn Arg Met Tyr Asp Val Leu His Glu
705                 710                 715                 720

Thr Ile Glu Asn Asp Phe Pro Lys Phe Leu Gly Lys Ile Phe Ala Phe
                725                 730                 735

Leu Ala Asn Pro Gly Leu Ile Ile Pro Ala Ile Leu Leu Met Phe Leu
                740             745                 750

Ala Ile Tyr Tyr Leu Asn Ser Val Ser Lys Ser Leu Ser Arg Ala Asn
        755                 760                 765

Ala Gln Leu Arg Lys Lys Ile Gln Ala Leu Arg Glu Val Glu Lys Asn
        770                 775                 780

His Lys Ser Ile Lys Gly Lys Ala Ile Val Thr Tyr Ser Glu Asp Thr
785                 790                 795                 800

Ile Lys Asn Ser Ser Lys Asn Ala Thr Gln Ile His Leu Thr Lys Glu
                805                 810                 815

Glu Pro Thr Ser His Ser Ser Ser Gln Ile Gln Thr Leu Asp Lys Lys
                820                 825                 830

Ala Gln Gly Pro His Thr Ser Ser Thr Glu Gly Gly Ala Ser Pro Ser
                835                 840                 845

Thr Ser Trp His His Val Gly Ser Gln Pro Pro Arg Gly Arg Arg Asp
                850                 855                 860

Ser Gly Gln Pro Gln Ser Gln Thr Tyr Thr Gly Arg Ser Pro Ser Gly
865                 870                 875                 880

Lys Arg Thr Gln Arg Pro His Asn
                885
```